US009610266B2

(12) United States Patent
Jackson et al.

(10) Patent No.: US 9,610,266 B2
(45) Date of Patent: Apr. 4, 2017

(54) SMALL MOLECULE INHIBITORS OF RNA BINDING MOTIF (RBM) PROTEINS FOR THE TREATMENT OF ACUTE CELLULAR INJURY

(71) Applicant: University of Pittsburgh—Of the Commonwealth System of Higher Education, Pittsburgh, PA (US)

(72) Inventors: Travis Corey Jackson, Pittsburgh, PA (US); Jonathan D. Verrier, Pittsburgh, PA (US); Patrick Kochanek, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 14/401,088

(22) PCT Filed: May 14, 2013

(86) PCT No.: PCT/US2013/040995
§ 371 (c)(1),
(2) Date: Nov. 13, 2014

(87) PCT Pub. No.: WO2013/173370
PCT Pub. Date: Nov. 21, 2013

(65) Prior Publication Data
US 2015/0141488 A1   May 21, 2015

Related U.S. Application Data

(60) Provisional application No. 61/646,928, filed on May 15, 2012.

(51) Int. Cl.
*A61K 31/185* (2006.01)
*C12N 15/113* (2010.01)
(Continued)

(52) U.S. Cl.
CPC .......... *A61K 31/185* (2013.01); *A61K 31/167* (2013.01); *A61K 31/192* (2013.01);
(Continued)

(58) Field of Classification Search
None
See application file for complete search history.

(56) References Cited

FOREIGN PATENT DOCUMENTS

| DE | WO 2008107211 A2 * | 9/2008 | .......... C07C 229/74 |
|----|---|---|---|
| DE | 102007063056 | 2/2009 | |
| EP | 2439200 | 4/2012 | |

OTHER PUBLICATIONS

Danziger et al., Automated Site-directed Drug Design: A General Algorithm for Knowledge Acquisition about Hydrogen-Bonding Regions at Protein Surfaces, Mar. 22, 1989, The Royal Society, Proceedings of the Royal Society of London.Series B, Biological Sciences, vol. 236, No. 1283, p. 101-113.*
(Continued)

*Primary Examiner* — San-Ming Hui
*Assistant Examiner* — Andrew Lee
(74) *Attorney, Agent, or Firm* — Klarquist Sparkman, LLP

(57) ABSTRACT

A method of treating a cellular injury in a subject comprising administering to a subject in need thereof, a therapeutically effective amount of a compound of formula I:
(Continued)

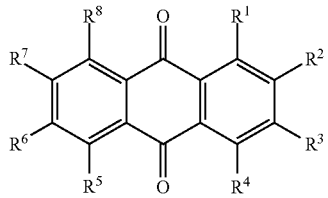

wherein at least one of $R^1$-$R^8$ is a sulfonic acid, a carboxylic acid, a phosphonic acid, a pharmaceutically acceptable salt of a sulfonic acid, a pharmaceutically acceptable salt of a carboxylic acid, a pharmaceutically acceptable salt of a phosphonic acid, a sulfonate ester, a carboxylate acid ester, or a phosphonate ester; and the remaining $R^1$-$R^8$ are each independently selected from hydrogen, halo, hydroxyl, nitro, nitroso, amino, substituted amino, alkyl, substituted alkyl, alkenyl, substituted alkenyl, alkynyl, substituted alkynyl, alkoxy, substituted alkoy, alkenyloxy, substituted alkenyloxy, alkynyloxy, substituted alkynyloxy, cycloalkyl, substituted cycloalkyl, cycloalkenyl, substituted cycloalkenyl, cycloalkynyl, substituted cycloalkynyl, cycloalkyloxy, substituted cycloalkyloxy, heterocyclyl, substituted heterocyclyl, heterocyclyloxy, substituted heterocyclyloxy, heterocyclylthio, substituted heterocyclylthio, cyano, acyl, acylamino, acyloxy, aminocarbonyl, aminocarbonylamino, aminothiocarbonylamino, aminocarbonyloxy, aminosulfonyl, sulfonylamino, aryl, substituted aryl, aryloxy, substituted aryloxy, arylthio, substituted arylthio, alkylthio, substituted alkylthio, cycloalkylthio, substituted cycloalkylthio, cycloalkenylthio, substituted cycloalkenylthio, thiol, heteroaryl, substituted heteroaryl, heteroaryloxy, substituted heteroaryloxy, heteroarylthio, substituted heteroarylthio, sulfonyl, or sulfonyloxy.

7 Claims, 27 Drawing Sheets

(51) Int. Cl.
| | | |
|---|---|---|
| A61K 31/167 | (2006.01) | |
| A61K 31/192 | (2006.01) | |
| A61K 31/44 | (2006.01) | |
| A61K 31/4418 | (2006.01) | |
| A61K 31/52 | (2006.01) | |
| A61K 31/551 | (2006.01) | |
| A61K 31/713 | (2006.01) | |

(52) U.S. Cl.
CPC .......... *A61K 31/44* (2013.01); *A61K 31/4418* (2013.01); *A61K 31/52* (2013.01); *A61K 31/551* (2013.01); *A61K 31/713* (2013.01); *C12N 15/113* (2013.01); *C12N 2310/14* (2013.01); *C12N 2310/531* (2013.01)

(56) References Cited

OTHER PUBLICATIONS

Chip et al., "The RNA-binding protein RBM3 is involved in hypothermia induced neuroprotection," *Neurobiology of Disease* 43:388-396, Apr. 17, 2011.
Farina et al., "Targeting zinc finger domains with small molecules: solution structure and binding studies of the RanBP2-type zinc finger of RBM5," *Chembiochem.* 12(18):2837-2845, Dec. 16, 2011.
Fushimi et al., "Up-regulation of the proapoptotic caspase 2 splicing isoform by a candidate tumor suppressor, RBM5," *PNAS* 105(41):15708-15713, Oct. 14, 2008.
Huwyler et al., "Receptor Mediated Delivery of Daunomycin Using Immunoliposomes: Pharmacokinetics and Tissue Distribution in the Rat," *Journal of Pharmacology and Experimental Therapeutics* 282(3):1541-1546, Sep. 1, 1997.
Jackson et al., "Anthraquinone-2-sulfonic acid (AQ2S) is a Novel Neurotherapeutic Agent," *Cell Death and Disease* 4:e451, published online Jan. 10, 2013.
Kado et al., "Human hematopoietic prostaglandin D synthase inhibitor complex structures" *Journal of Biochemistry* 151(4):447-455, Apr. 4, 2012.
Liang et al., "Prostaglandin $D_2$ mediates neuronal protection via the DP1 receptor," *Journal of Neurochemistry* 92:477-486, 2005, published online Dec. 14, 2004.
Liu et al., "Protective role of hematopoietic prostaglandin D synthase in transient focal cerebral ischemia in mice," *Neuroscience* 163(1):296-307, Sep. 29, 2009.
Saleem et al., "PGD2 DP1 receptor protects brain from ischemia-reperfusion injury," *Eur J Neurosci* 26(1):73-78, Jul. 2007, published online Jun. 16, 2007.
Taniguchi et al., "Prostaglandin $D_2$ Protects Neonatal Mouse Brain from Hypoxic Ischemic Injury," *The Journal of Neuroscience* 27(16):4303-4312, Apr. 18, 2007.
International Search Report issued for PCT/US2013/040995, dated Sep. 5, 2013.
Written Opinion of the International Searching Authority issued for PCT/US2013/040995, dated Sep. 5, 2013.

* cited by examiner

FIG. 4
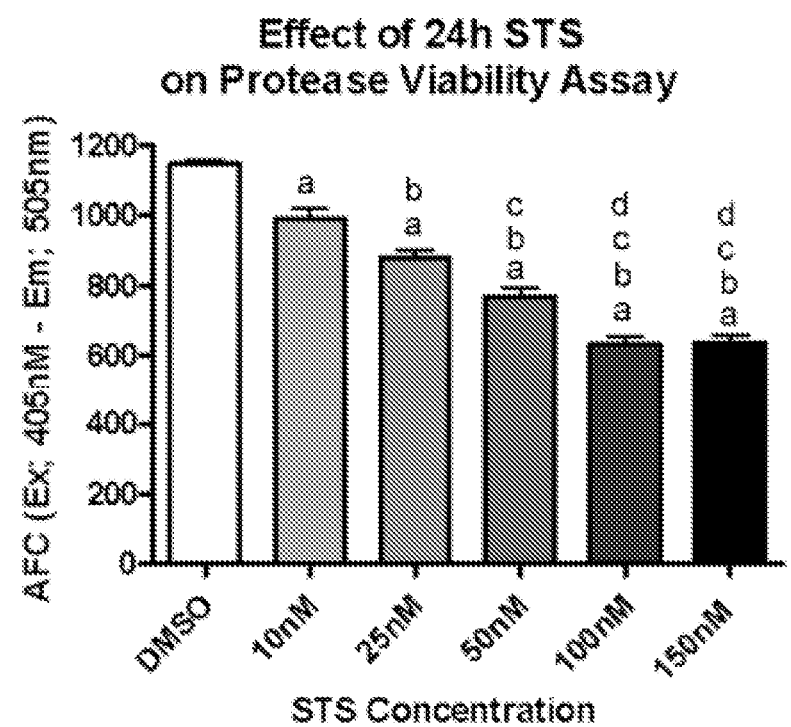
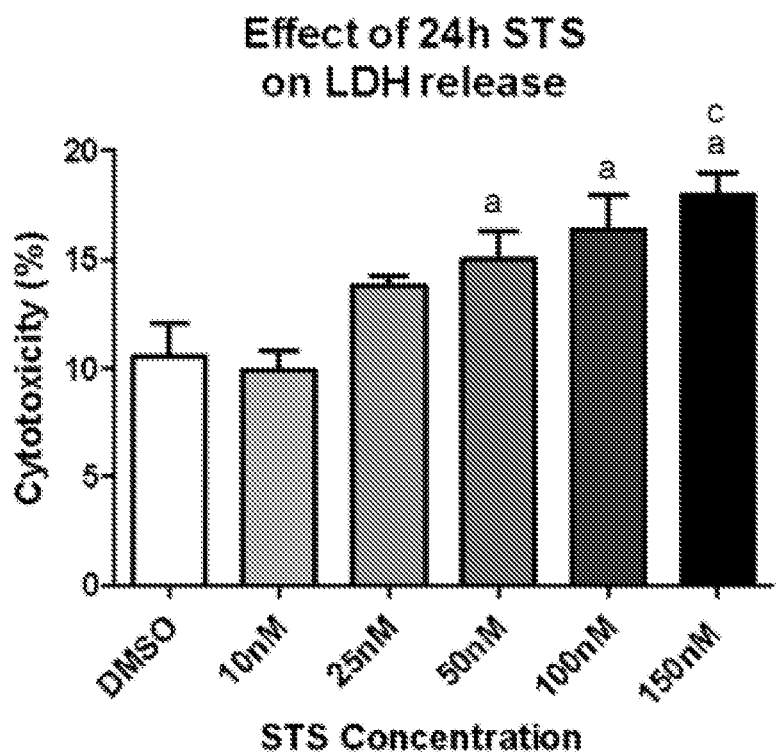

FIG. 7
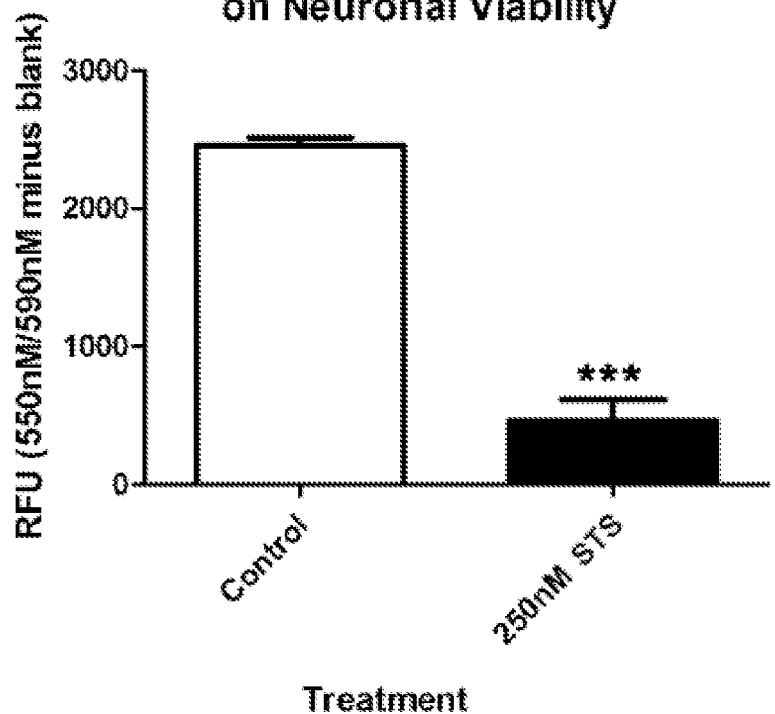
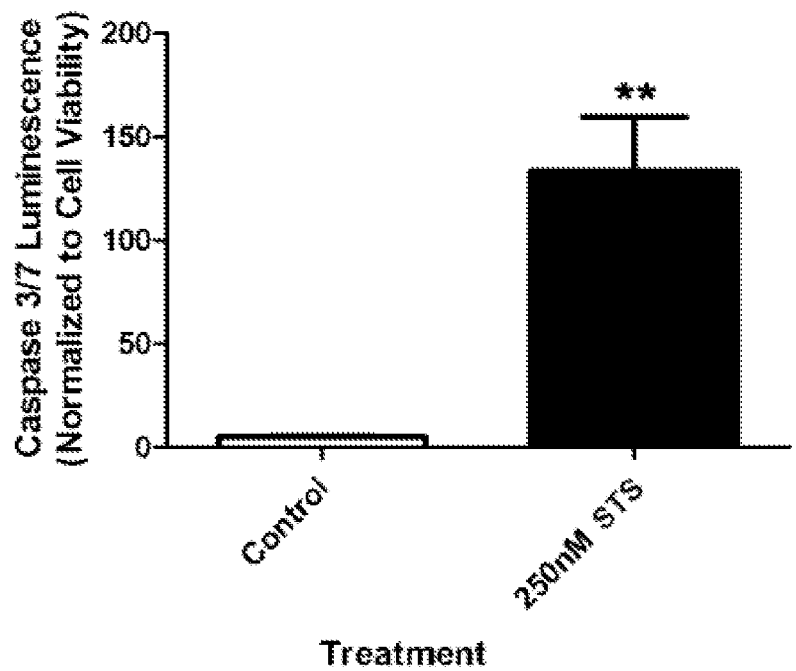

FIG. 11
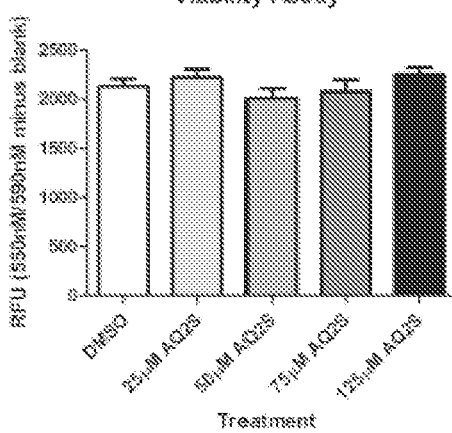
Effect of AQ2S on CellTiter Blue Viability Assay
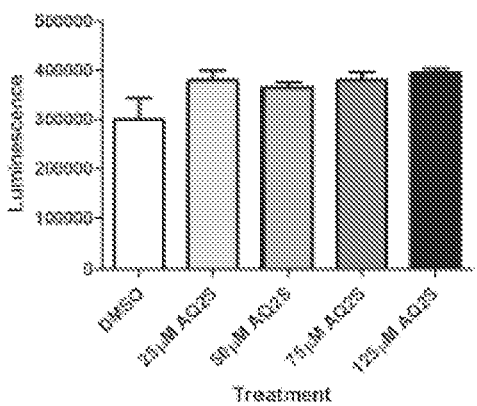
Effect of AQ2S on Luminescence Viability Assay
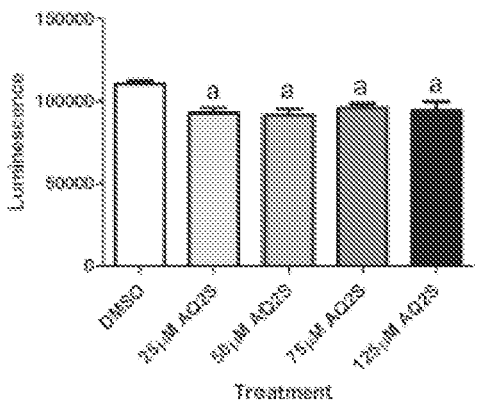
Effect of AQ2S on Luminescence: Interaction With CellTiter Blue FIG. 14
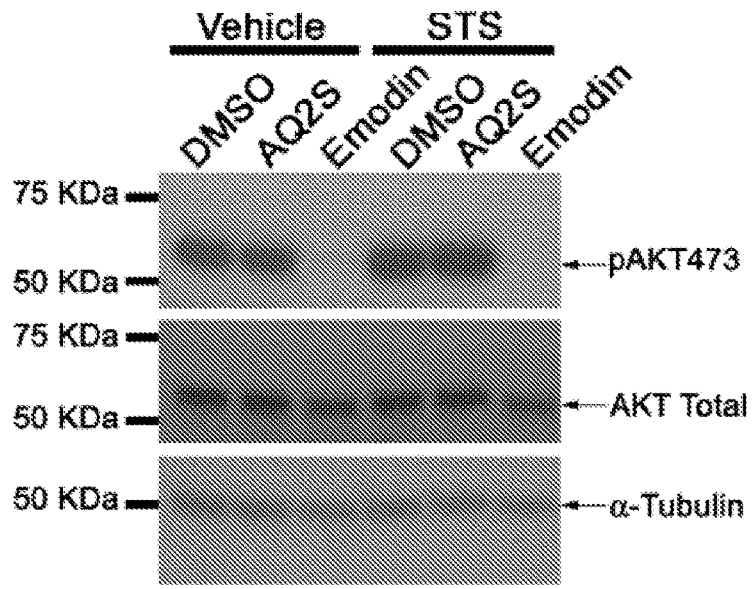
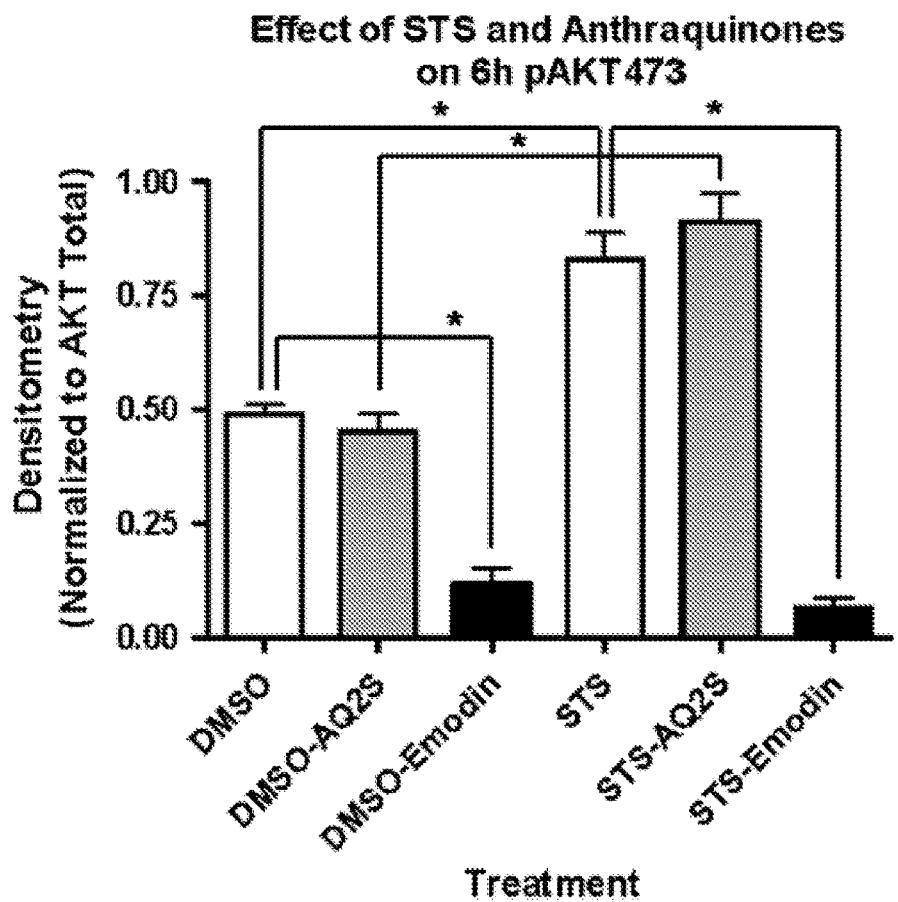

FIG. 15
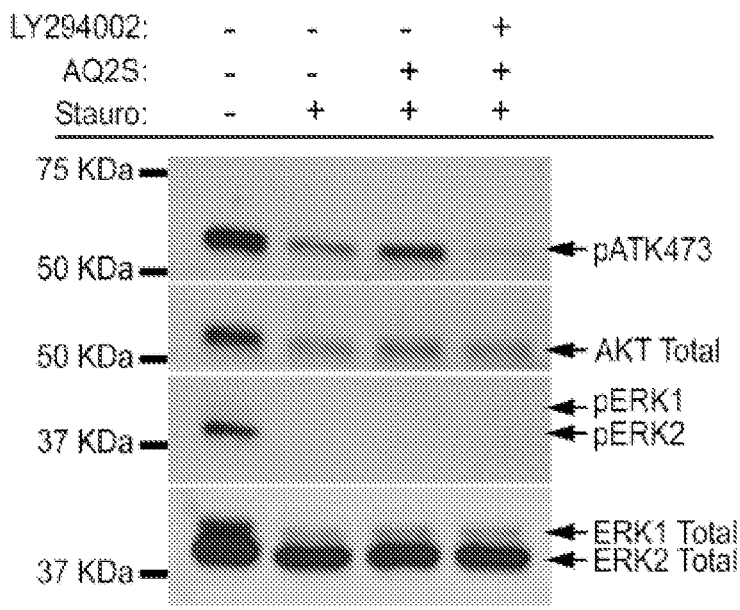
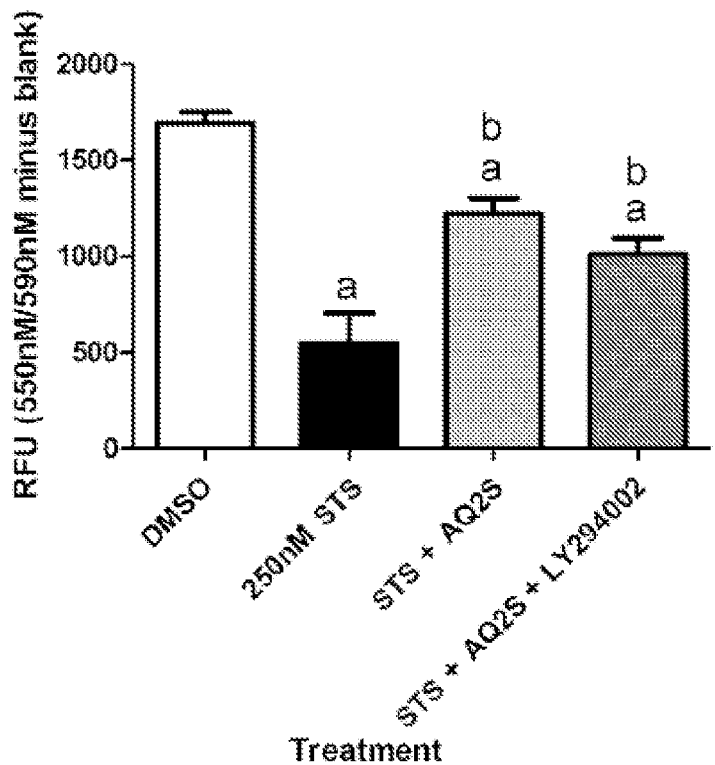

FIG. 18
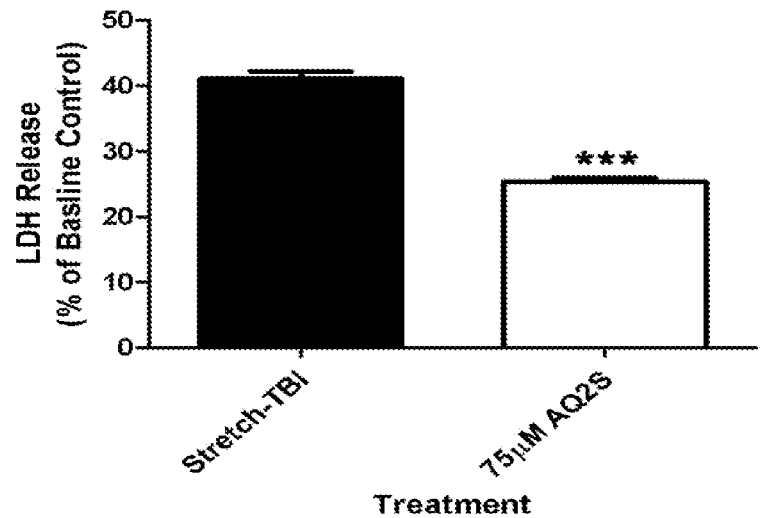
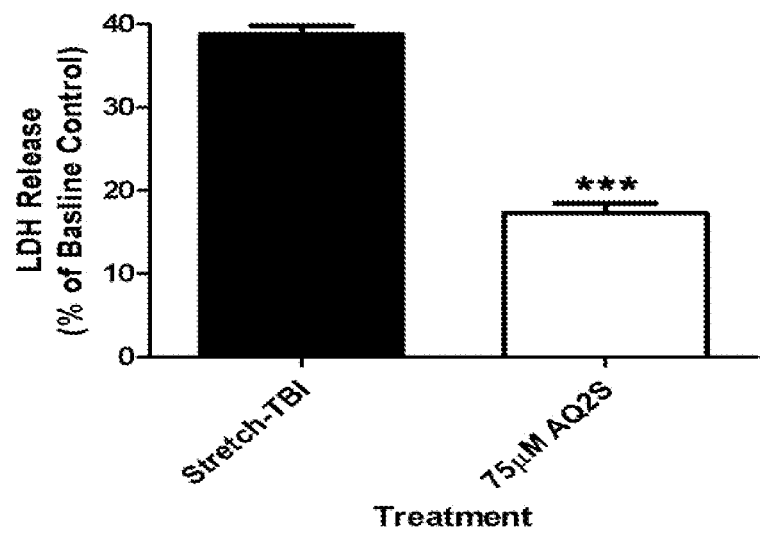

FIG. 19
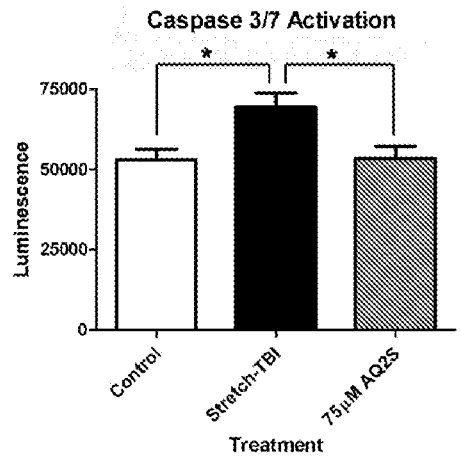
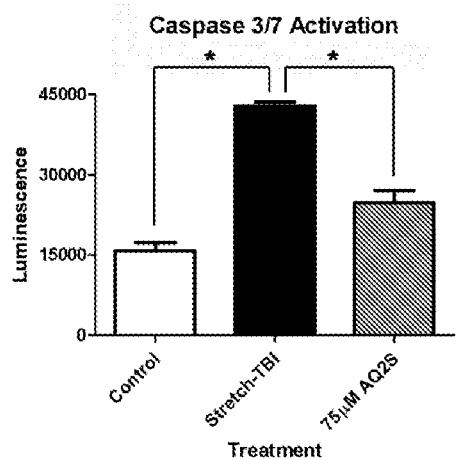
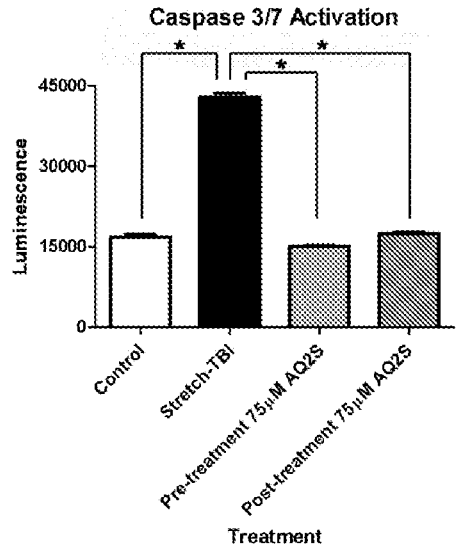

FIG. 26
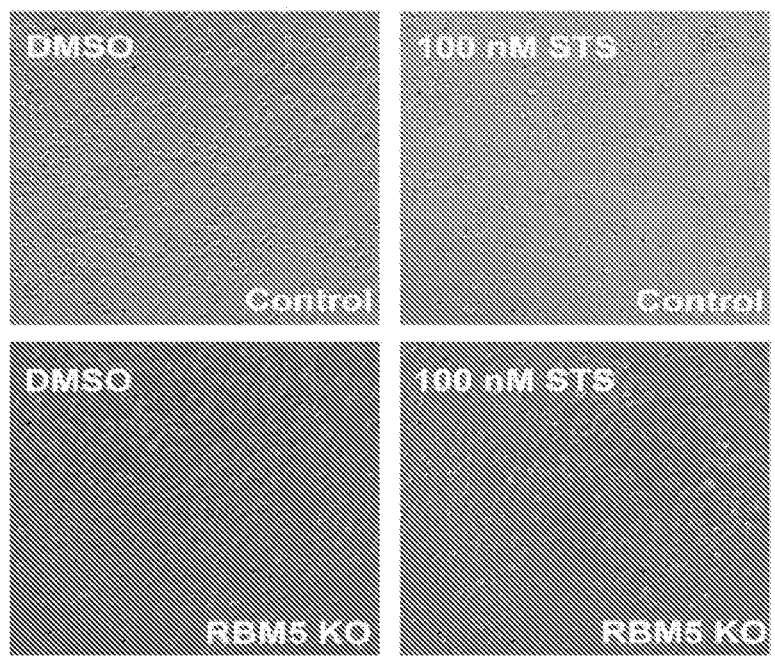
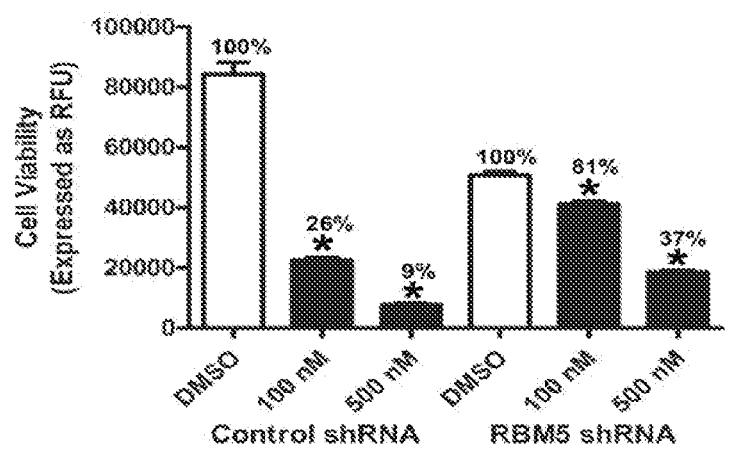

FIG. 28
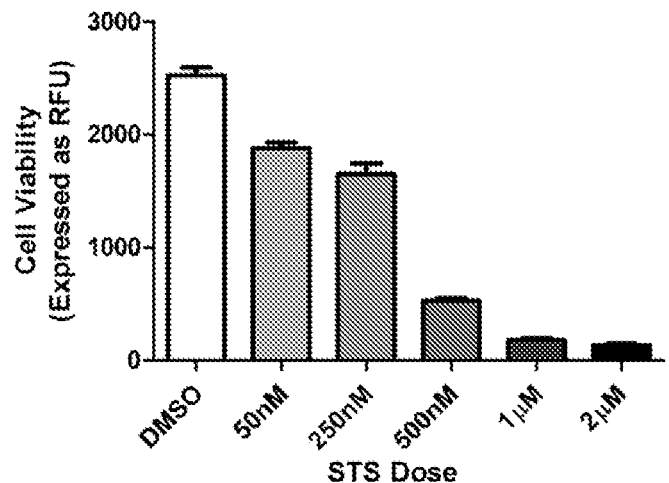
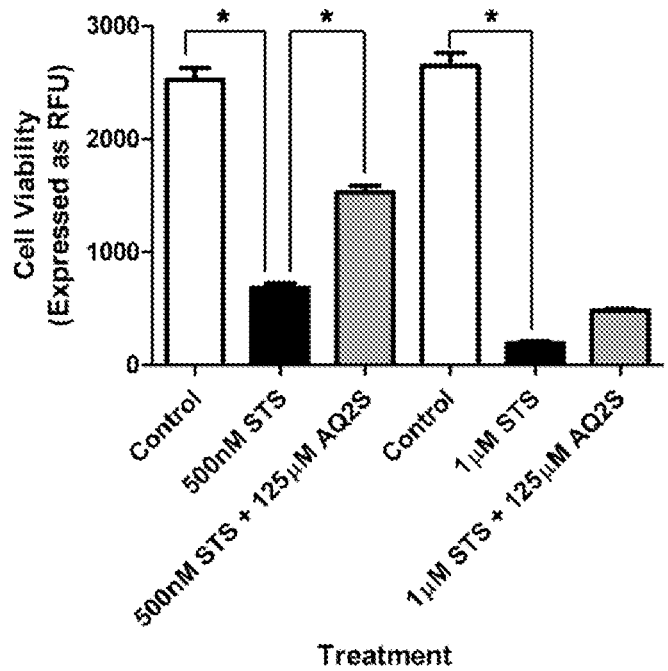

SMALL MOLECULE INHIBITORS OF RNA BINDING MOTIF (RBM) PROTEINS FOR THE TREATMENT OF ACUTE CELLULAR INJURY

CROSS REFERENCE TO RELATED APPLICATIONS

This is the U.S. National Stage of International Application No. PCT/US2013/040995, filed May 14, 2013, which was published in English under PCT Article 21(2), which in turn claims the benefit of U.S. Provisional Application No. 61/646,928, filed May 15, 2012, and incorporated herein by reference in their entirety.

ACKNOWLEDGMENT OF GOVERNMENT SUPPORT

This invention was made with government support under grant number NS070003 awarded by the National Institute for Health. The government has certain rights in the invention.

FIELD

The present invention relates generally to the field of pharmaceutical formulations and specifically to formulations of small molecules that inhibit cell, tissue, and organ death.

BACKGROUND

Quinones are a unique class of organic compound identified by the presence of a cyclic diketone structure. The simplest example is 1,4-benzequinone (BQ). BQ consists of a single benzene ring flanked by 2 ketone [R—C(=O)] groups at the 1st and 4th carbons. 9-10-anthraquinone (AQ) is only slightly more complex. AQ is derived from the 3 ring aromatic structure anthracene. Anthraquinones constitute a large and diverse subgroup within the quinone superfamily. Anthraquinone based drugs are clinically used as laxatives and chemotherapeutic agents. In addition, they show promise as treatments for malaria, and multiple sclerosis.

Natural anthraquinones have a brilliant range of colors and were used as dyeing agents since antiquity. Recent studies show that some natural anthraquinones exhibit unique medicinal properties. Preliminary evidence suggests that the natural anthraquinone emodin (6-methyl-1,3,8-trihydroxyanthraquinone) is an especially promising neuroprotective drug with possible indications for the treatment of chronic neurodegenerative disease. Emodin prevents neuronal death in cell culture models of degenerative pathology. Alzheimer's disease is characterized by excessive accumulation of two key pathological proteins in the brain, beta-amyloid (Aβ plaques) and the microtubule associated tau (tau tangles). The dysfunctional regulation and hyperphosphorylation of tau leads to protein misfolding. In turn, tau proteins dimerize to form cytotoxic tangles in afflicted neurons. (i.e. tauopathy). Pickhardt et al. used genetically modified neuroblastoma cells, engineered to overpress aberrant tau, and screened for tauopathy inhibitors. Emodin efficiently inhibited tau aggregation in this system.

The anti-aggregation activity of emodin may be a trait shared amongst many anthraquinone derivatives. Colombo et al. found that the chemotherapeutic anthraquinones mitoxantrone and pixantrone prevent aggregation of toxic (soluble) $A\beta_{1-42}$. Furthermore, pixantrone inhibited $A\beta_{1-42}$ tocixity in neuroblastoma cells. Similarly, Convertino et al. investigated the structural intercalation of AQ with β-amyloid sheets, and found that it efficiently inhibited aggregation of the $A\beta_{1-40}$ fragment.

Incubation of pathological Aβ induces cell death of primary neurons. Liu et al. reported that 24 hour emodin pretreatment protected cultured cortical neurons from subsequent injury induced by incubation with the highly toxic $A\beta_{25-35}$ fragment. The beneficial effect of emodin was blocked by addition of the phosphatidylinositol-3-kinase (PI3K)/AKT inhibitor LY294002. The result indicates that PI3K/AKT is an important survival mechanism activated by emodin in this study. However, it is unclear if emodin directly activates AKT signaling. Arguing against a direct role for AKT activation in this model, $A\beta_{25-35}$ is reported to robustly inhibit endogenous AKT activity in both primary neurons and cerebrovascular endothelial cells. Therefore, emodin (as an aggregate inhibitor) may simply relieve $A\beta_{25-35}$ induced AKT repression. Moreover, studies in cancer cells report that emodin is a potent PI3K inhibitor ($IC_{50}$ 3.3 μM); certainly a contradiction to an AKT activator.

The challenges of treating acute brain injury are uniquely different from managing a chronic neurodegenerative disease. The mechanisms of neuronal death are highly variable (depending on type of brain injury), and the time window for therapeutic intervention is often short. Limited evidence supports a protective role for emodin (and related natural anthraquinone compounds) in ischemic brain injury. Oxidative damage is an important component of acute ischemic injury. Pretreament of cultured cortical neurons with emodin prevents subsequent injury by 150 μM $H_2O_2$. Similarly, cotreatment with 50 μM danthron (1,8-dihydroxyanthraquinone) protects mixed neuron-glial cultures in five models of oxidative injury. Neuroprotection was observed in the presence of $A\beta_{25-35}$, $Fe^{3+}$ peroxidation, buthionine sulfoximine (BSO) induced glutathione depletion, nitric oxide radical production, or $H_2O_2$. Interestingly, in this same study, the authors report danthron was ineffective against zinc toxicity, xanthine/xanthine oxidase $O_2$ radicals, NMDA, kainate, STS, or dextromethorphan. These results show that danthron is preferentially neuroprotective in models of progressive oxidative stress.

Finally, a recent study found that the emodin analogue, emodin-8-O-beta-D-glucoside, was able to pass through the blood brain barrier (BBB) and reduce infarct volume after focal cerebral ischemia. The authors report a significant rise in the activity of endogenous antioxidant superoxide dismutase (SOD) following experimental drug treatment. Consistent with increased SOD, malondialdehyde (MDA), a measure of lipid peroxidation, was decreased in emodin-glucoside treated animals. Altogether the evidence suggests that natural anthraquinones boost antioxidant defenses, which may contribute to their neuroprotective actions in models of acute brain injury.

Pretreatment with natural anthraquinones promote antioxidant survival mechanisms and reduce oxidative stress. However, the time course to induce this protective response is unknown. In clinical practice, most opportunities to treat acute brain injury are restricted to the post-injury period. Emodin has not been tested using an in vitro post-treatment study design. For anthraquinones to be viable drug candidates in the field of acute brain injury, evidence should support their efficacy when administered after injury.

SUMMARY

Disclosed herein in one embodiment is a method of treating a cellular injury in a subject comprising administering to a subject in need thereof, a therapeutically effective amount of a compound of formula I:

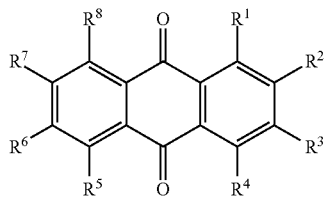

wherein at least one of $R^1$-$R^8$ is a sulfonic acid, a carboxylic acid, a phosphonic acid, a pharmaceutically acceptable salt of a sulfonic acid, a pharmaceutically acceptable salt of a carboxylic acid, a pharmaceutically acceptable salt of a phosphonic acid, a sulfonate ester, a carboxylate acid ester, or a phosphonate ester; and the remaining $R^1$-$R^8$ are each independently selected from hydrogen, halo, hydroxyl, nitro, nitroso, amino, substituted amino, alkyl, substituted alkyl, alkenyl, substituted alkenyl, alkynyl, substituted alkynyl, alkoxy, substituted alkoxy, alkenyloxy, substituted alkenyloxy, alkynyloxy, substituted alkynyloxy, cycloalkyl, substituted cycloalkyl, cycloalkenyl, substituted cycloalkenyl, cycloalkynyl, substituted cycloalkynyl, cycloalkyloxy, substituted cycloalkyloxy, heterocyclyl, substituted heterocyclyl, heterocyclyloxy, substituted heterocyclyloxy, heterocyclylthio, substituted heterocyclylthio, cyano, acyl, acylamino, acyloxy, aminocarbonyl, aminocarbonylamino, aminothiocarbonylamino, aminocarbonyloxy, aminosulfonyl, sulfonylamino, aryl, substituted aryl, aryloxy, substituted aryloxy, arylthio, substituted arylthio, alkylthio, substituted alkylthio, cycloalkylthio, substituted cycloalkylthio, cycloalkenylthio, substituted cycloalkenylthio, thiol, heteroaryl, substituted heteroaryl, heteroaryloxy, substituted heteroaryloxy, heteroarylthio, substituted heteroarylthio, sulfonyl, or sulfonyloxy.

Also disclosed herein is a method for treating a central nervous system injury or neurodegenerative disease in a subject comprising administering to a subject in need thereof a therapeutically effective amount of a compound of formula I.

Further disclosed herein is a method for treating a central nervous system injury or neurodegenerative disease in a subject comprising administering to a subject in need thereof a therapeutically effective amount of an RNA binding motif (RBM) protein inhibitor.

An additional disclosed embodiment is a pharmaceutical composition comprising: a therapeutically effective amount of a compound of formula I; and a pharmaceutically acceptable additive.

Further disclosed is a method of treating brain injury or disease by administering a sulfonated anthraquinone.

Additionally disclosed is a method of treating or preventing brain injury or disease by administering an RBM inhibitor.

The foregoing will become more apparent from the following detailed description, which proceeds with reference to the accompanying figures.

BRIEF DESCRIPTION OF THE DRAWINGS

FIG. 4 is concentration dependent STS induced decrease in neuronal viability (protease activity assay) and increase in cytotoxicity (LDH release).

FIG. 7 is the effect of STS on neuronal viability and caspase 3/7 activity.

FIG. 11 is the effect of AQ2S on fluorescent and luminescent viability assays.

FIG. 14 is the blocking of acute STS-induced AKT activation by emodin, measured in primary rat neurons.

FIG. 15 is the AQ2S-mediated neuroprotection while blocking AKT in primary rat cortical neurons.

FIG. 18 is the effect of AQ2S on stretch injury induced neuronal lactate dehydrogenase (LDH) release in primary rat cortical neurons.

FIG. 19 is the effect of AQ2S on stretch injury induced caspase 3/7 activity in primary rat cortical neurons.

FIG. 26 is the protection by RBM5 knock-out of N2a cells from STS induced cell death.

FIG. 28 is the protection of human heart cells by AQ2S from STS induced injury.

DETAILED DESCRIPTION

A. Terminology

Figure 1:
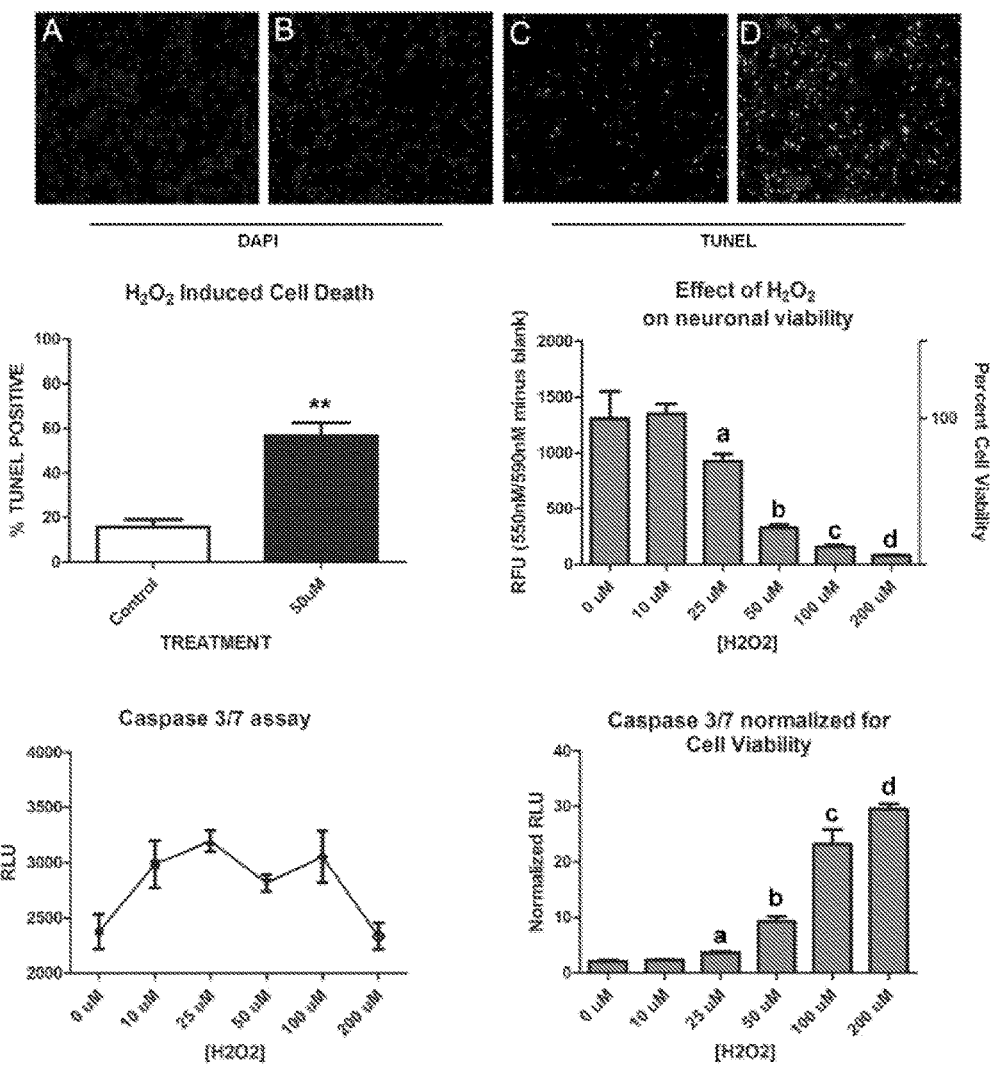
FIG. 1 is acute oxidative injury inducing neuronal death over 24 hours.

As used herein, the singular terms "a," "an," and "the" include plural referents unless context clearly indicates otherwise. Also, as used herein, the term "comprises" means "includes."

Although methods and materials similar or equivalent to those described herein can be used in the practice or testing of the present disclosure, suitable methods and materials are described below. In addition, the materials, methods, and examples are illustrative only and not intended to be limiting.

To facilitate review of the various examples of this disclosure, the following explanations of specific terms are provided:

"Alkyl" refers to monovalent saturated aliphatic hydrocarbonyl groups having from 1 to 10 carbon atoms and preferably 1 to 6 carbon atoms. This term includes, by way of example, linear and branched hydrocarbonyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Substituted alkyl" refers to an alkyl group having from 1 to 5 hydrogens replaced with substituents selected, for example, from alkoxy, substituted alkoxy, acyl, acylamino, acyloxy, amino, substituted amino, aminocarbonyl, aminocarbonylamino, aminothiocarbonylamino, aminocarbonyloxy, aminosulfonyl, aryl, substituted aryl, aryloxy, substituted aryloxy, arylthio, substituted arylthio, carboxyl, carboxyl ester, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, alkynyl, substituted alkynyl, cycloalkynyl, substituted cycloalkynyl halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, sulfonyl, sulfonyloxy, thiol, alkylthio, and substituted alkylthio, wherein said substituents are defined herein.

In some embodiments, the alkyl has 1 to 3 of the aforementioned groups. In other embodiments, the alkyl has 1 to 2 of the aforementioned groups.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like.

"Substituted alkoxy" refers to the group —O-(substituted alkyl), wherein substituted alkyl is as defined herein.

"Alkenyloxy" refers to the group —O-alkenyl, wherein alkenyl is as defined herein.

"Substituted alkenyloxy" refers to the group —O-(substituted alkenyl), wherein substituted alkenyl is as defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Acyl includes the "acetyl" group $CH_3C(O)$—.

"Acylamino" refers to the groups —$NR^{20}C(O)$alkyl, —$NR^{20}C(O)$substituted alkyl, —$NR^{20}C(O)$cycloalkyl, —$NR^{20}C(O)$substituted cycloalkyl, —$NR^{20}C(O)$cycloalkenyl, —$NR^{20}C(O)$substituted cycloalkenyl, —$NR^{20}C(O)$alkenyl, —$NR^{20}C(O)$substituted alkenyl, —$NR^{20}C(O)$alkynyl, —$NR^{20}C(O)$substituted alkynyl, —$NR^{20}C(O)$aryl, —$NR^{20}C(O)$substituted aryl, —$NR^{20}C(O)$heteroaryl, —$NR^{20}C(O)$substituted heteroaryl, —$NR^{20}C(O)$heterocyclic, and —$NR^{20}C(O)$substituted heterocyclic, wherein $R^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O) O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group —$NH_2$.

"Substituted amino" refers to the group —$NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, where one of $R^{21}$ and $R^{22}$ is sulfonyl, and wherein $R^{21}$ and $R^{22}$ are optionally joined together with the nitrogen bound thereto to form a heterocyclic or substituted heterocyclic group, provided that $R^{21}$ and $R^{22}$ are not both hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, sulfonyl, substituted heteroaryl, heterocyclic, and substituted heterocyclic are as defined herein.

"Aminocarbonyl" refers to the group —$C(O)NR^{21}R^{22}$ wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{20}$C(O)NR$^{21}$R$^{22}$, wherein R$^{20}$ is hydrogen or alkyl and R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonylamino" refers to the group —NR$^{20}$C(S)NR$^{21}$R$^{22}$, wherein R$^{20}$ is hydrogen or alkyl and R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonyloxy" refers to the group —O—C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like), provided that the point of attachment is through an atom of the aromatic aryl group. Preferred aryl groups include phenyl and naphthyl.

"Substituted aryl" refers to aryl groups having 1 to 5 hydrogens replaced with substituents independently selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminocarbonylamino, aminothiocarbonylamino, aminocarbonyloxy, aminosulfonyl, aryl, substituted aryl, aryloxy, substituted aryloxy, arylthio, substituted arylthio, carboxyl, carboxyl ester, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, sulfonyl, sulfonyloxy, thiol, alkylthio, and substituted alkylthio, wherein said substituents are as defined herein. In some embodiments, the aryl has 1 to 3 of the aforementioned groups. In other embodiments, the aryl has 1 to 2 of the aforementioned groups.

"Aryloxy" refers to the group —O-aryl, wherein aryl is as defined herein, including, by way of example, phenoxy, naphthoxy, and the like.

"Substituted aryloxy" refers to the group —O-(substituted aryl), wherein substituted aryl is as defined herein.

"Arylthio" refers to the group —S-aryl, wherein aryl is as defined herein. In other embodiments, sulfur may be oxidized to —S(O)— or —SO$_2$— moieties. The sulfoxide may exist as one or more stereoisomers.

"Substituted arylthio" refers to the group —S-(substituted aryl), wherein substituted aryl is as defined herein. In other embodiments, sulfur may be oxidized to —S(O)— or —SO$_2$— moieties. The sulfoxide may exist as one or more stereoisomers.

"Alkenyl" refers to monovalent unsaturated hydrocarbonyl groups having from 2 to 6 carbon atoms and preferably 2 to 4 carbon atoms and having at least 1 and preferably from 1 to 2 sites of unsaturation. Such groups are exemplified by vinyl, allyl, but-3-en-1-yl, and the like.

"Substituted alkenyl" refers to alkenyl groups having from 1 to 3 substituents selected from, for example, alkoxy, substituted alkoxy, acyl, acylamino, acyloxy, amino, substituted amino, aminocarbonyl, aminocarbonylamino, aminothiocarbonylamino, aminocarbonyloxy, aminosulfonyl, aryl, substituted aryl, aryloxy, substituted aryloxy, arylthio, substituted arylthio, carboxyl, carboxyl ester, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, sulfonyl, sulfonyloxy, thiol, alkylthio, and substituted alkylthio, wherein said substituents are as defined herein and with the proviso that any hydroxy substitution is not attached to a vinyl (unsaturated) carbon atom. In some embodiments, the alkenyl has 1 to 2 of the aforementioned groups.

"Alkynyl" refers to monovalent unsaturated hydrocarbonyl groups having from 2 to 6 carbon atoms and preferably 2 to 3 carbon atoms and having at least 1 and preferably from 1 to 2 sites of triple bond unsaturation.

"Substituted alkynyl" refers to alkynyl groups having from 1 to 3 substituents selected from, for example, alkoxy, substituted alkoxy, acyl, acylamino, acyloxy, amino, substituted amino, aminocarbonyl, aminocarbonylamino, aminothiocarbonylamino, aminocarbonyloxy, aminosulfonyl, aryl, substituted aryl, aryloxy, substituted aryloxy, arylthio, substituted arylthio, carboxyl, carboxyl ester, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, sulfonyl, sulfonyloxy, thiol, alkylthio, and substituted alkylthio, wherein said substituents are as defined herein and with the proviso that any hydroxy or thiol substitution is not attached to an acetylenic carbon atom. In some embodiments, the alkynyl has 1 to 2 of the aforementioned groups.

"Alkynyloxy" refers to the group —O-alkynyl, wherein alkynyl is as defined herein. Alkynyloxy includes, by way of example, ethynyloxy, propynyloxy, and the like.

"Carboxyl" or "carboxy" or "carboxylic acid" refers to —COOH or salts thereof.

"Sulfonic acid" refers to —SO$_2$OH or salts thereof.

"Carboxyl ester" or "carboxy ester" or "carboxylate ester" refers to the groups —C(O)O-alkyl, —C(O)O— substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Sulfonate ester" or "sulfonic acid ester" refers to the groups —SO$_2$O-alkyl, —SO$_2$O-substituted alkyl, —SO$_2$O-alkenyl, —SO$_2$O-substituted alkenyl, —SO$_2$O-alkynyl, —SO$_2$O-substituted alkynyl, —SO$_2$O-aryl, —SO$_2$O-substituted aryl, —SO$_2$O-cycloalkyl, —SO$_2$O-substituted cycloalkyl, —SO$_2$O-cycloalkenyl, —SO$_2$O-substituted cycloalkenyl, —SO$_2$O-heteroaryl, —SO$_2$O-substituted heteroaryl, —SO$_2$O-heterocyclic, and —SO$_2$O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Phosphonic acid" refers to the group —P(=O)(OH)$_2$ or salts thereof.

"Phosphonic acid ester" or "Phosphonate ester" refers to the group —P(=O)(OR$^{21}$)(OR$^{22}$), wherein R$^{21}$ and R$^{22}$ are each independently selected from the group consisting of alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like.

"Cycloalkenyl" refers to non-aromatic cyclic alkyl groups of from 3 to 10 carbon atoms having single or multiple rings and having at least one double bond and preferably from 1 to 2 double bonds.

"Cycloalkynyl" refers to non-aromatic cycloalkyl groups of from 5 to 10 carbon atoms having single or multiple rings and having at least one triple bond.

"Substituted cycloalkyl," "substituted cycloalkenyl," and "substituted cycloalkynyl" refer to a cycloalkyl, cycloalkenyl, or cycloalkynyl group having from 1 to 5 substituents selected from the group consisting of oxo, thioxo, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminocarbonylamino, aminothiocarbonylamino, aminocarbonyloxy, aminosulfonyl, aryl, substituted aryl, aryloxy, substituted aryloxy, arylthio, substituted arylthio, carboxyl, carboxyl ester, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, sulfonyl, sulfonyloxy, thiol, alkylthio, and substituted alkylthio, wherein said substituents are as defined herein, provides that any hydroxy or thiol substitution is not attached to an unsaturated carbon atom. In some embodiments, the cycloalkyl or cycloalkenyl has 1 to 3 of the aforementioned groups. In some embodiments, the cycloalkyl group may have multiple condensed rings (e.g. tetrahydronaphthyl or tetrahydroanthacenyl), provided that the point of attachment is through an atom of the nonaromatic ring.

"Cycloalkyloxy" refers to —O-cycloalkyl.

"Substituted cycloalkyloxy" refers to —O-(substituted cycloalkyl).

"Cycloalkylthio" refers to —S-cycloalkyl. In other embodiments, sulfur may be oxidized to —S(O)— or —SO$_2$— moieties. The sulfoxide may exist as one or more stereoisomers.

"Substituted cycloalkylthio" refers to —S-(substituted cycloalkyl). In other embodiments, sulfur may be oxidized to —S(O)—, or —SO$_2$— moieties. The sulfoxide may exist as one or more stereoisomers.

"Cycloalkenyloxy" refers to —O-cycloalkenyl.

"Substituted cycloalkenyloxy" refers to —O-(substituted cycloalkenyl).

"Cycloalkenylthio" refers to —S-cycloalkenyl. In other embodiments, sulfur may be oxidized to sulfinyl or sulfonyl moieties. The sulfoxide may exist as one or more stereoisomers.

"Substituted cycloalkenylthio" refers to —S-(substituted cycloalkenyl). In other embodiments, sulfur may be oxidized to —S(O)— or —SO$_2$— moieties. The sulfoxide may exist as one or more stereoisomers.

"Halo" or "halogen" refers to fluoro, chloro, bromo, and iodo and is preferably fluoro or chloro.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen, and sulfur within the ring. Such heteroaryl groups can have a single ring (e.g., pyridinyl or furyl) or multiple condensed rings (e.g., indolizinyl or benzothienyl), wherein the condensed rings may or may not be aromatic and/or contain a heteroatom, provided that the point of attachment is through an atom of the aromatic heteroaryl group. In one embodiment, the nitrogen and/or sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5 substituents selected from the group consisting of the same group of substituents defined for substituted aryl. In some embodiments, the heteroaryl has 1 to 3 of the aforementioned groups. In other embodiments, the heteroaryl has 1 to 2 of the aforementioned groups.

"Heteroaryloxy" refers to —O-heteroaryl.

"Substituted heteroaryloxy" refers to the group —O-(substituted heteroaryl).

"Heteroarylthio" refers to the group —S-heteroaryl. In other embodiments, sulfur may be oxidized to —S(O)— or —SO$_2$— moieties. The sulfoxide may exist as one or more stereoisomers.

"Substituted heteroarylthio" refers to the group —S-(substituted heteroaryl). In other embodiments, sulfur may be oxidized to —S(O)— or —SO$_2$— moieties. The sulfoxide may exist as one or more stereoisomers.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 15 ring atoms, including 1 to 4 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In one embodiment, the nitrogen and/or sulfur atom(s) of the heterocyclic group are optionally oxidized to provide for the N-oxide, —S(O)—, or —SO$_2$— moieties.

"Substituted heterocyclic," "substituted heterocycloalkyl," and "substituted heterocyclyl" refer to heterocyclyl groups that are substituted with from 1 to 5 of the same substituents as defined for substituted cycloalkyl. In some embodiments, the heterocyclyl has 1 to 3 of the aforementioned groups.

"Heterocyclyloxy" refers to the group —O-heterocyclyl.

"Substituted heterocyclyloxy" refers to the group —O-(substituted heterocyclyl).

"Heterocyclylthio" refers to the group —S-heterocyclyl. In other embodiments, sulfur may be oxidized to —S(O)— or —SO$_2$— moieties. The sulfoxide may exist as one or more stereoisomers.

"Substituted heterocyclylthio" refers to the group —S-(substituted heterocyclyl). In other embodiments, sulfur may be oxidized to —S(O)— or —SO$_2$— moieties. The sulfoxide may exist as one or more stereoisomers.

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

"Nitro" refers to the group —NO$_2$.

"Nitroso" refers to the group —NO.

"Oxo" refers to the atom (=O).

"Sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cylcoalkyl, —SO$_2$-cycloalkenyl, —SO$_2$- substituted cylcoalkenyl, —SO$_2$-aryl, —SO$_2$-substituted aryl, —SO$_2$-heteroaryl, —SO$_2$-substituted heteroaryl, —SO$_2$-heterocyclic, and —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes groups such as methyl-SO$_2$—, phenyl-SO$_2$—, and 4-methylphenyl-SO$_2$—.

"Sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cylcoalkyl, —OSO$_2$-cycloalkenyl, —OSO$_2$-substituted cylcoalkenyl, —OSO$_2$-aryl, —OSO$_2$-substituted aryl, —OSO$_2$-heteroaryl, —OSO$_2$-substituted heteroaryl, —OSO$_2$-heterocyclic, and —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thiol" refers to the group —SH.

"Alkylthio" refers to the group —S-alkyl, wherein alkyl is as defined herein. In other embodiments, sulfur may be oxidized to —S(O)—. The sulfoxide may exist as one or more stereoisomers.

"Substituted alkylthio" refers to the group —S-(substituted alkyl), wherein substituted alkyl is as defined herein. In other embodiments, sulfur may be oxidized to —S(O)—. The sulfoxide may exist as one or more stereoisomers.

"Stereoisomer" and "stereoisomers" refer to compounds that differ in the chirality of one or more stereocenters. Stereoisomers include enantiomers and diastereomers. A "therapeutically effective amount" refers to a quantity of a specified agent sufficient to achieve a desired effect in a subject being treated with that agent. For example, a therapeutically amount may be an amount of a PI3K inhibitor agent or mTOR inhibitor that is sufficient to inhibit radiation-induced apoptosis.

Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition.

The term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

A "therapeutically effective amount" refers to a quantity of a specified agent sufficient to achieve a desired effect in a subject being treated with that agent. For example, a therapeutically amount may be an amount of a FBXO3 inhibitor that is sufficient to inhibit inflammation in a subject. Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease, for example, in a subject who is at risk for a disease such as cancer.

"Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition. In certain embodiments disclosed herein, the treatment inhibits inflammation in a subject.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's *Pharmaceutical Sciences*, Mack Publishing Co., Easton, Pa. (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, $C_{1-4}$ alkyl, or $C_{1-4}$ alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocyclyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

B. Compounds

Disclosed therein are novel methods for using anthraquinone compounds for treating cellular injury and disease. A general formula for the anthraquinone compounds is given by formula I below:

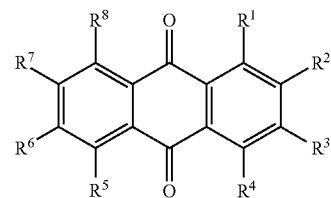

wherein at least one of $R^1$-$R^8$ is a sulfonic acid, a carboxylic acid, a phosphonic acid, a pharmaceutically acceptable salt of a sulfonic acid, a pharmaceutically acceptable salt of a carboxylic acid, a pharmaceutically acceptable salt of a phosphonic acid, a sulfonate ester, a carboxylate acid ester, or a phosphonate ester. The remaining $R^1$-$R^8$ are each independently selected from hydrogen, halo, hydroxyl, nitro, nitroso, amino, substituted amino, alkyl, substituted alkyl, alkenyl, substituted alkenyl, alkynyl, substituted alkynyl, alkoxy, substituted alkoxy, alkenyloxy, substituted alkenyloxy, alkynyloxy, substituted alkynyloxy, cycloalkyl, substituted cycloalkyl, cycloalkenyl, substituted cycloalkenyl, cycloalkynyl, substituted cycloalkynyl, cycloalkyloxy, substituted cycloalkyloxy, heterocyclyl, substituted heterocyclyl, heterocyclyloxy, substituted heterocyclyloxy, heterocyclylthio, substituted heterocyclylthio, cyano, acyl, acylamino, acyloxy, aminocarbonyl, aminocarbonylamino, aminothiocarbonylamino, aminocarbonyloxy, aminosulfonyl, sulfonylamino, aryl, substituted aryl, aryloxy, substituted aryloxy, arylthio, substituted arylthio, alkylthio, substituted alkylthio, cycloalkylthio, substituted cycloalkylthio, cycloalkenylthio, substituted cycloalkenylthio, thiol, heteroaryl, substituted heteroaryl, heteroaryloxy, substituted heteroaryloxy, heteroarylthio, substituted heteroarylthio, sulfonyl, or sulfonyloxy.

In some embodiments at least one of $R^1$-$R^8$ is a sulfonic acid, a pharmaceutically acceptable salt of a sulfonic acid, or a sulfonate ester. In some embodiments at least one of $R^1$-$R^8$ is a sulfonic acid, a pharmaceutically acceptable salt of a sulfonic acid, or a sulfonate ester, and the remaining $R^1$-$R^8$ groups are all hydrogen. In some particular embodiments $R^2$ is a sulfonic acid, a pharmaceutically acceptable salt of a sulfonic acid, or a sulfonate ester. In one preferred embodiment the compound of formula I is anthraquinone-2-sulfonic acid (AQ2S), or a pharmaceutically acceptable salt thereof, wherein $R^2$ is a sulfonic acid or salt thereof, and $R^1$ and $R^3$-$R^8$ are all hydrogen.

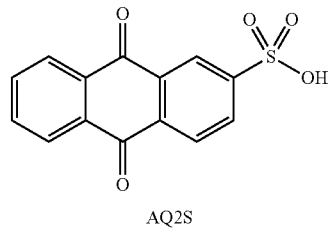 [SMILES: O=C1c2ccccc2C(=O)c2cc(S(=O)(=O)O)ccc21]

AQ2S

In other embodiments the compound of formula I is anthraquinone-1-sulfonic acid, anthraquinone-3-sulfonic acid, anthraquinone-4-sulfonic acid, anthraquinone-5-sulfonic acid, anthraquinone-6-sulfonic acid, anthraquinone-7-sulfonic acid, anthraquinone-8-sulfonic acid, or a pharmaceutically acceptable salt thereof.

In other embodiments at least one of $R^1$-$R^8$ is a carboxylic acid, a pharmaceutically acceptable salt of a carboxylic acid, or a carboxyl ester. In some embodiments at least one of $R^1$-$R^8$ is a carboxylic acid, a pharmaceutically acceptable salt of a carboxylic acid, or a carboxylate ester, and the remaining $R^1$-$R^8$ groups are all hydrogen. In some particular embodiments $R^2$ is a carboxylic acid, a pharmaceutically acceptable salt of a sulfonic acid, or a carboxyl ester. In one preferred embodiment the compound of formula I is anthraquinone-2-carboxylic acid, or a pharmaceutically acceptable salt thereof, wherein $R^2$ is a carboxylic acid or salt thereof, and $R^1$ and $R^3$-$R^8$ are all hydrogen.

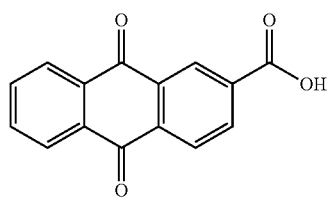

Anthraquinone-2-carboxylic acid

In other embodiments the compound of formula I is anthraquinone-1-carboxylic acid, anthraquinone-3-carboxylic acid, anthraquinone-4-carboxylic acid, anthraquinone-5-carboxylic acid, anthraquinone-6-carboxylic acid, anthraquinone-7-carboxylic acid, anthraquinone-8-carboxylic acid, or a pharmaceutically acceptable salt thereof.

Also disclosed herein are embodiments of the compounds of formula I that are RNA Binding Motif (RBM) inhibitors. Other known RBM inhibitors include:

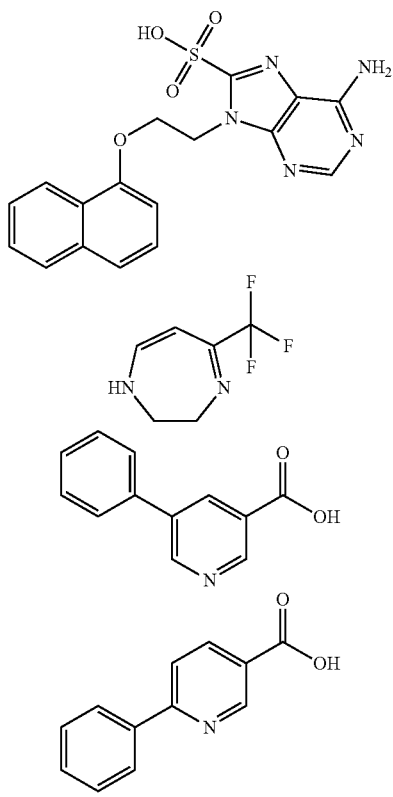

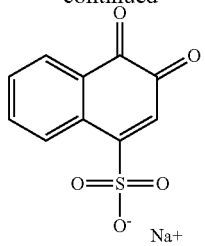

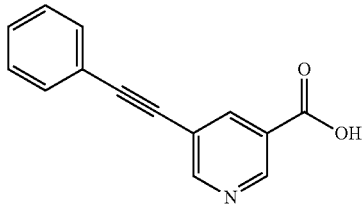

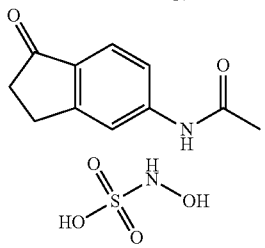

C. Pharmaceutical Compositions and Methods

Anthraquinones are a class of both natural and synthetic chemical compounds that are chemically derived from anthracene. Work disclosed herein evaluated whether natural (e.g., emodin, rhein, and aloin) and synthetic (e.g., anthraquinone-2-sulfonic acid sodium salt; AQ2S) small-molecule anthraquinones displayed neuroprotective effects in experimental models of acute brain injury and chemical toxicity. Surprisingly, post-injury treatment with synthetic anthraquinones effectively prevented cell death in primary rat cultures following exposure to severe oxidative stress or stretch-trauma injury. In addition, synthetic anthraquinones prevented cell death induced by the potent toxin staurosporine.

While not wishing to be bound by theory, it is currently believed that AQ2S and related compounds may achieve their protective effects, in part, by interacting with an RNA binding motif (RBM) protein—specifically one or several of the pro-apoptotic zinc-finger containing RBMs. In preliminary studies, AQ2S was demonstrated to be a selective and potent target of the zinc-finger domain in pro-apoptotic RBM5 and inhibits its function (Farina B, Fattorusso R, Pellecchia M (2011). Targeting zinc finger domains with small molecules: solution structure and binding studies of the RanBP2-type zinc finger of RBM5. Chembiochem 12(18): 2837-2845).

The compounds of formula I prevent death of primary neurons. The mechanism(s) of neuroprotection include, but are not limited to, caspase inhibition and AKT activation. In addition, the compounds are effective when given after injury (post-treatment). This is important and highly relevant for treatment protocols of acute CNS injuries in clinical scenarios such as traumatic brain injury, stroke, and cardiac arrest, and also for the treatment of ischemia, for example, in the brain, heart or kidneys.

In certain embodiments, the compounds and compositions disclosed herein may be useful for treating a subject with a traumatic central nervous system injury, more particularly, a traumatic brain injury. A traumatic injury to the CNS is characterized by a physical impact and/or overpressure wave to the central nervous system. For example, a traumatic brain injury results when the brain is subjected to a physical force that results in progressive neuronal cell damage and/or cell death. A traumatic brain injury may result from a blow to the head and manifest as either an open or closed injury. A traumatic brain injury may also result from proximity to an explosion or blast overpressure wave (bTBI). Severe brain damage can occur from lacerations, skull fractures, subarachnoid hemorrhage (SAH), and conversely, even in the absence of external signs of head injury. Furthermore, TBI induced CNS damage can be exacerbated by coexisting injuries (poly-trauma) such as, but not limited to, bleeding induced hemorrhagic shock, and frequent clinical complications (e.g. sepsis). Accordingly, the methods can be used to treat a traumatic brain injury, including, blunt traumas, penetrating traumas, as well as, blast traumas.

In accordance with the methods disclosed herein, the compounds and compositions may be used to promote a positive therapeutic response with respect to the traumatic central nervous system injury. For example, the treatment may be any improvement in the subject having the traumatic CNS injury including improved morphological recovery (i.e., enhanced tissue viability) and/or behavioral recovery, and/or beneficial changes in serum/CSF biomarkers indicative of CNS, kidney, or heart improvements that would be understood by those skilled in the art. The improvement can be characterized as an increase in either the rate and/or the extent of behavioral and anatomical recovery following the traumatic CNS injury. The improvement can also be characterized as a change (decrease or increase) in a clinically accepted physiological surrogate of health. Examples include a decreased or increase in serum/CSF biomarkers that predict worsening or improved outcomes, respectively. Another example of improvement include an observed decrease in high (>20 mmHg) intracranial pressure—a predictor of poor outcome in TBI patients.

In certain embodiments, the compounds and compositions disclosed herein may be useful for treating a neurodegenerative disease involving lesioned or traumatized neurons, such as chronic traumatic encephalopathy (CTE), seizures, traumatic lesions of peripheral nerves, the medulla, and/or the spinal cord, cerebral ischemic neuronal damage, neuropathy and especially peripheral neuropathy, peripheral nerve trauma or injury, ischemic stroke, acute brain injury, acute spinal cord injury, nervous system tumors, multiple sclerosis, exposure to neurotoxins, metabolic diseases such as diabetes or renal dysfunctions and damage caused by infectious agents, neurodegenerative disorders including Alzheimer's disease, Huntington's disease, Parkinson's disease, Parkinson-Plus syndromes, progressive Supranuclear Palsy (Steele-Richardson-Olszewski Syndrome), Olivopontocerebellar Atrophy (OPCA), Shy-Drager Syndrome (multiple systems atrophy), Guamanian parkinsonism dementia complex, amyotrophic lateral sclerosis, or any other congenital or neurodegenerative disease, and memory impairment connected to dementia.

Neurodegeneration is the progressive loss of neurons in the central nervous system, including the brain. As used herein, "neuroprotection" is the arrest and/or reverse progression of neurodegeneration following an acute brain injury or associated with a neurodegenerative disease. Multiple physiological events lead to the neurodegeneration of the CNS tissues following a traumatic CNS injury. These events include, for example, cerebral edema, destruction of vascular integrity, increase in the immune and inflammatory response, demyelinization, and lipid peroxidation. Hence, the methods disclose herein also find use in reducing and/or preventing the physiological events leading to neurodegeneration. Specifically, the methods may reduce or eliminate neuronal cell death, edema, ischemia, and enhancing brain tissue parenchyma viability following a traumatic injury to the central nervous system.

The compounds disclosed herein may be administered to a subject having an acute brain injury. As defined herein, the subject can be any mammal, preferably a human. In specific embodiments, the human is an adult (over 18 years of age), while in other embodiments, the human is a child (under 18 years of age). The child can be a neonate, infant, toddler, pre-pubescent or post-pubescent and range in age from about birth, 1 month to about 2 year, about 1 year to about 5 years, about 4 years to about 9 years, about 8 years to about 14, or about 13 to about 18 years of age. In addition, the human can be about 55 to 60, 60 to 65, 65 to 70, 70 to 75, 75 to 80, 80 to 85, 85 to 90, 90 to 95 or older.

The amount of the compound may be administered in a dosage unit that is effective in the treatment or prevention of neuronal damage that follows injury to the CNS and hence, elicits a neuroprotective effect.

The compounds disclosed herein may be associated with at least one additive or excipient that facilitates transport across the blood brain barrier. Illustrative examples include polyethylene glycol substrates, immunoliposomes, and an avidin-biotin vector.

Another aspect of the disclosure includes pharmaceutical compositions prepared for administration to a subject and which include a therapeutically effective amount of one or more of the compounds disclosed herein. The therapeutically effective amount of a disclosed compound will depend on the route of administration, the species of subject and the physical characteristics of the subject being treated. Specific factors that can be taken into account include disease severity and stage, weight, diet and concurrent medications. The relationship of these factors to determining a therapeutically effective amount of the disclosed compounds is understood by those of skill in the art.

Pharmaceutical compositions for administration to a subject can include at least one further pharmaceutically acceptable additive such as carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical compositions disclosed herein include those formed from pharmaceutically acceptable salts and/or solvates of the disclosed compounds. Pharmaceutically acceptable salts include those derived from pharmaceutically acceptable inorganic or organic bases and acids. Particular disclosed compounds possess at least one basic group that can form acid-base salts with acids. Examples of basic groups include, but are not limited to, amino and imino groups. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid. In particular, suitable salts include those derived from alkali metals such as potassium and sodium, alkaline earth metals such as calcium and magnesium, among numerous other acids well known in the pharmaceutical art.

Certain compounds include at least one acidic group that can form an acid-base salt with an inorganic or organic base. Examples of salts formed from inorganic bases include salts of the presently disclosed compounds with alkali metals such as potassium and sodium, alkaline earth metals, including calcium and magnesium and the like. Similarly, salts of acidic compounds with an organic base, such as an amine (as used herein terms that refer to amines should be understood to include their conjugate acids unless the context clearly indicates that the free amine is intended) are contemplated, including salts formed with basic amino acids, aliphatic amines, heterocyclic amines, aromatic amines, pyridines, guanidines and amidines. Of the aliphatic amines, the acyclic aliphatic amines, and cyclic and acyclic di- and tri-alkyl amines are particularly suitable for use in the disclosed compounds. In addition, quaternary ammonium counterions also can be used.

Particular examples of suitable amine bases (and their corresponding ammonium ions) for use in the present compounds include, without limitation, pyridine, N,N-dimethylaminopyridine, diazabicyclononane, diazabicycloundecene, N-methyl-N-ethylamine, diethylamine, triethylamine, diisopropylethylamine, mono-, bis- or tris-(2-hydroxyethyl)amine, 2-hydroxy-tert-butylamine, tris(hydroxymethyl)methylamine, N,N-dimethyl-N-(2-hydroxyethyl)amine, tri-(2-hydroxyethyl)amine and N-methyl-D-glucamine. For additional examples of "pharmacologically acceptable salts," see Berge et al., *J. Pharm. Sci.* 66:1 (1977).

Compounds disclosed herein can be crystallized and can be provided in a single crystalline form or as a combination of different crystal polymorphs. As such, the compounds can be provided in one or more physical form, such as different crystal forms, crystalline, liquid crystalline or non-crystalline (amorphous) forms. Such different physical forms of the compounds can be prepared using, for example different solvents or different mixtures of solvents for recrystallization. Alternatively or additionally, different polymorphs can be prepared, for example, by performing recrystallizations at different temperatures and/or by altering cooling rates during recrystallization. The presence of polymorphs can be determined by X-ray crystallography, or in some cases by another spectroscopic technique, such as solid phase NMR spectroscopy, IR spectroscopy, or by differential scanning calorimetry.

The pharmaceutical compositions can be administered to subjects by a variety of mucosal administration modes, including by oral, rectal, intranasal, intrapulmonary, or transdermal delivery, or by topical delivery to other surfaces. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other alternative embodiments, the compound can be administered ex vivo by direct exposure to cells, tissues or organs originating from a subject.

To formulate the pharmaceutical compositions, the compound can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The compound can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The compound can be combined with the base or vehicle according to a variety of methods, and release of the compound can be by diffusion, disintegration of the vehicle, or associated formation of water channels. In some circumstances, the compound is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly (epsilon-caprolactone), poly(epsilon-aprolactone-CO-lactic acid), poly(epsilon.-aprolactone-CO-glycolic acid), poly (beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

The administration of the compound of the disclosure can be for either prophylactic or therapeutic purpose. When provided prophylactically, the compound is provided in advance of any symptom. The prophylactic administration of the compound serves to prevent or ameliorate any subsequent disease process. When provided therapeutically, the compound is provided at (or shortly after) the onset of a symptom of disease or infection.

For prophylactic and therapeutic purposes, the compound can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, dog, sheep, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the compound (for example, amounts that are effective to alleviate one or more symptoms of a targeted disease). In alternative embodiments, an effective amount or effective dose of the compound may simply inhibit or enhance one or more selected biological activities correlated with a disease or condition, as set forth herein, for either therapeutic or diagnostic purposes.

The actual dosage of the compound will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the compound for eliciting the desired activity or biological response in the subject. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and formulations of the disclosure is about 0.01 mg/kg body weight to about 20 mg/kg body weight, such as about 0.05 mg/kg to about 5 mg/kg body weight, or about 0.2 mg/kg to about 2 mg/kg body weight.

Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, intraosseous, or intranasal delivery versus intravenous or subcutaneous or intramuscular delivery. Dosage can also be adjusted based on the release rate of the administered formulation, for example, of an intrapulmonary spray versus powder, sustained release oral versus injected particulate or transdermal delivery formulations, and so forth.

The compounds disclosed herein may also be co-administered with an additional therapeutic agent. Such agents include, but are not limited to, another anti-inflammatory agent, an antimicrobial agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

The instant disclosure also includes kits, packages and multi-container units containing the herein described pharmaceutical compositions, active ingredients, and/or means for administering the same for use in the prevention and treatment of diseases and other conditions in mammalian subjects. Kits for diagnostic use are also provided. In one embodiment, these kits include a container or formulation that contains one or more of the compounds described herein. In one example, this component is formulated in a pharmaceutical preparation for delivery to a subject. The compound is optionally contained in a bulk dispensing container or unit or multi-unit dosage form. Optional dispensing means can be provided, for example a pulmonary or intranasal spray applicator. Packaging materials optionally include a label or instruction indicating for what treatment purposes and/or in what manner the pharmaceutical agent packaged therewith can be used.

EXAMPLES

Post-injury treatment with natural anthraquinones does not prevent $H_2O_2$-induced neuronal death. A sensitive $H_2O_2$ injury protocol was developed first (FIG. 1). Cortical neurons were harvested and grown in neurobasal media containing B27 in the presence of antioxidants for 3 days. Prior studies show that neurons do not require antioxidants to survive after the first 24 hours. Therefore, fresh neurobasal media was prepared without antioxidants (i.e., B27-AO) for subsequent media exchanges. At day-in-vitro (D.I.V.) 10-11, maintenance media was replaced with unsupplemented neurobasal (i.e., without B27) containing $H_2O_2$ and incubated for 35 minutes. Neurons were returned to fresh neurobasal/B27 (-AO) media, and cell viability measured 24 hours later. As expected, even low concentrations of $H_2O_2$ (25-50 µM) significantly increased TUNEL staining (FIG. 1A-E), significantly decreased cell viability (FIG. 1F), and increased caspase-3/7 activity (FIG. 1G-H). From these preliminary results, 40 µM $H_2O_2$ was selected as the optimal dose to screen neuroprotection of test compounds.

Insulin like growth factor-1 (IGF-1) potently stimulates IGF-1 receptor phosphorylation (FIG. 2A-Western Blot Insert), and is a well established in vitro and in vivo neuroprotectant. Importantly, $H_2O_2$ injury is one of the few cell death paradigms in which IGF-1 therapy is ineffective if given after the insult (post-treatment) but is effective before the insult (pretreatment). The mechanism(s) underlying this phenomenon involve $H_2O_2$-mediated inactivation of neuronal IGF-1 receptor signaling, and is prevented by co-treatment with minocycline. Because $H_2O_2$ injury induces major derangements in cell signaling, and pretreatment therapies are often futile in the context of acute brain injury, experiments were designed to test if the selected anthraquinones could prevent neuronal death applied after $H_2O_2$ injury. Consistent with previous literature, post-treatment with 100 ng/mL IGF-1 was ineffective at rescuing neurons from $H_2O_2$ injury (FIG. 2A-D). The natural anthraquinones rhein (FIG. 2A) and aloin (FIG. 2B) were also ineffective at any concentration tested 24 hours post-injury.

Unexpectedly, both 5 μM and 25 μM emodin (FIG. 2C) failed to protect neurons form $H_2O_2$. In addition, 50 μM emodin exacerbated cell death. Alternatively, 50 μM AQ2S significantly reduced $H_2O_2$ induced cell death (FIG. 2D). To validate the results, the worst and best anthraquinones (emodin vs. AQ2S) were compared on a caspase 3/7 activity assay. Compared to control injury, emodin significantly reduced caspase activity at all 3 concentrations (FIG. 2E). Similarly, AQ2S inhibited caspase 3/7 activity at both the 25 μM and 50 μM concentrations but not at the lowest 5 μM concentration (FIG. 2F).

Figure 3:
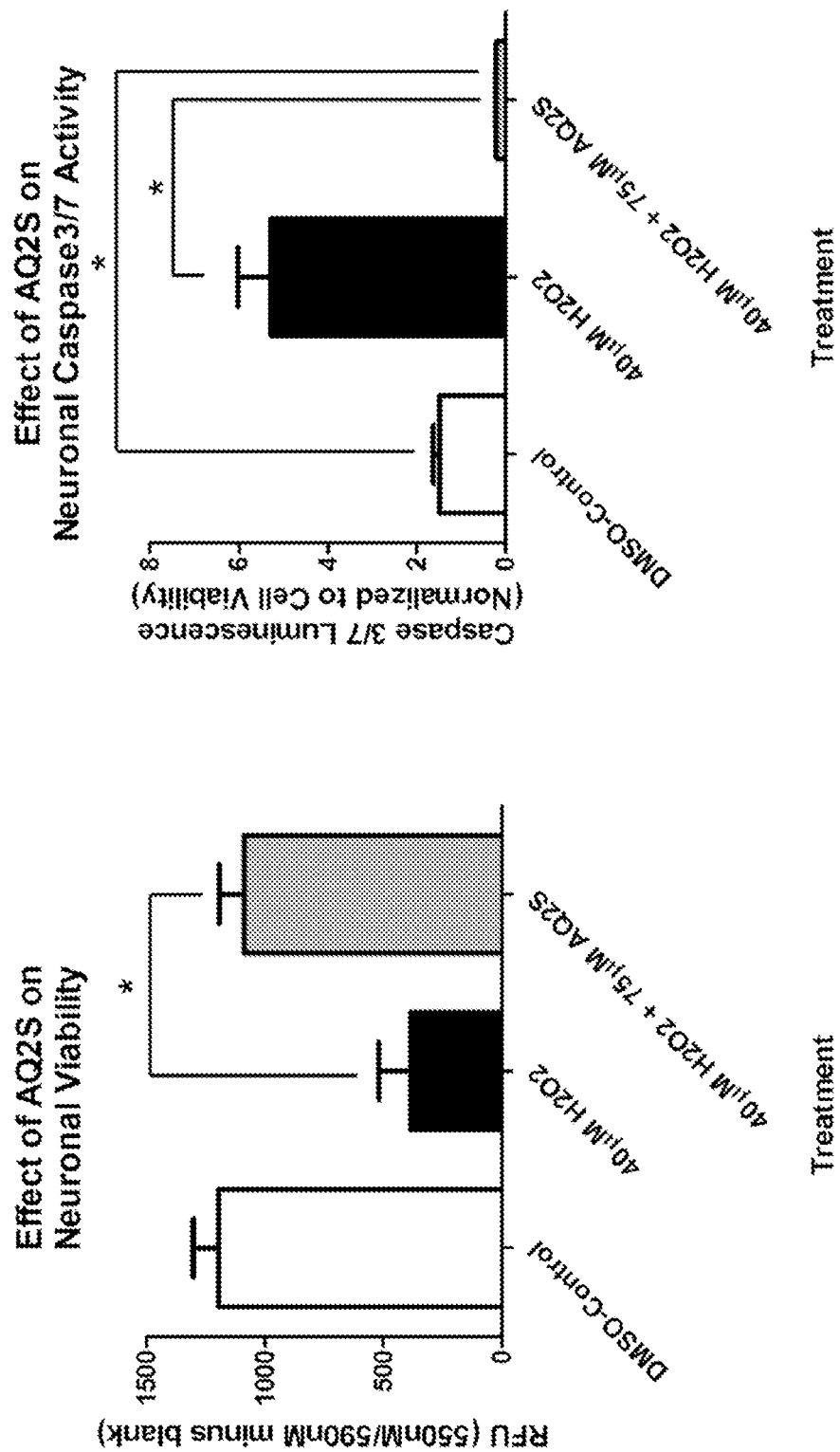
FIG. 3 is the enhanced protection with AQ2S of primary rat cortical neurons against $H_2O_2$.

AQ2S was the only compound able to inhibit cell death when given after $H_2O_2$ injury. Therefore efforts were focused on AQ2S to validate its neuroprotective actions. The $H_2O_2$ injury assay was repeated using a higher concentration of AQ2S. 75 μM AQ2S potently prevented cell death induced by 40 μM $H_2O_2$ measured 24 h after injury (FIG. 3A). Moreover, consistent with prior results, 75 μM AQ2S significantly inhibited caspase 3/7 activity below injured and non-injured levels (FIG. 3B).

AQ2S Prevents Classic STS-Induced Cell Death. STS is an established inducer of caspase-mediated apoptotic cell death in neurons. To further authenticate AQ2S as a novel neuroprotective compound, cortical neurons were subjected to STS injury±AQ2S. In preliminary dose—response experiments, it was found that 150 nM STS for 24 hours optimally decreased viability measured by a live-cell protease activity assay (FIG. 4A) and increased lactate dehydrogenase (LDH) release (FIG. 4B).

Figure 5:
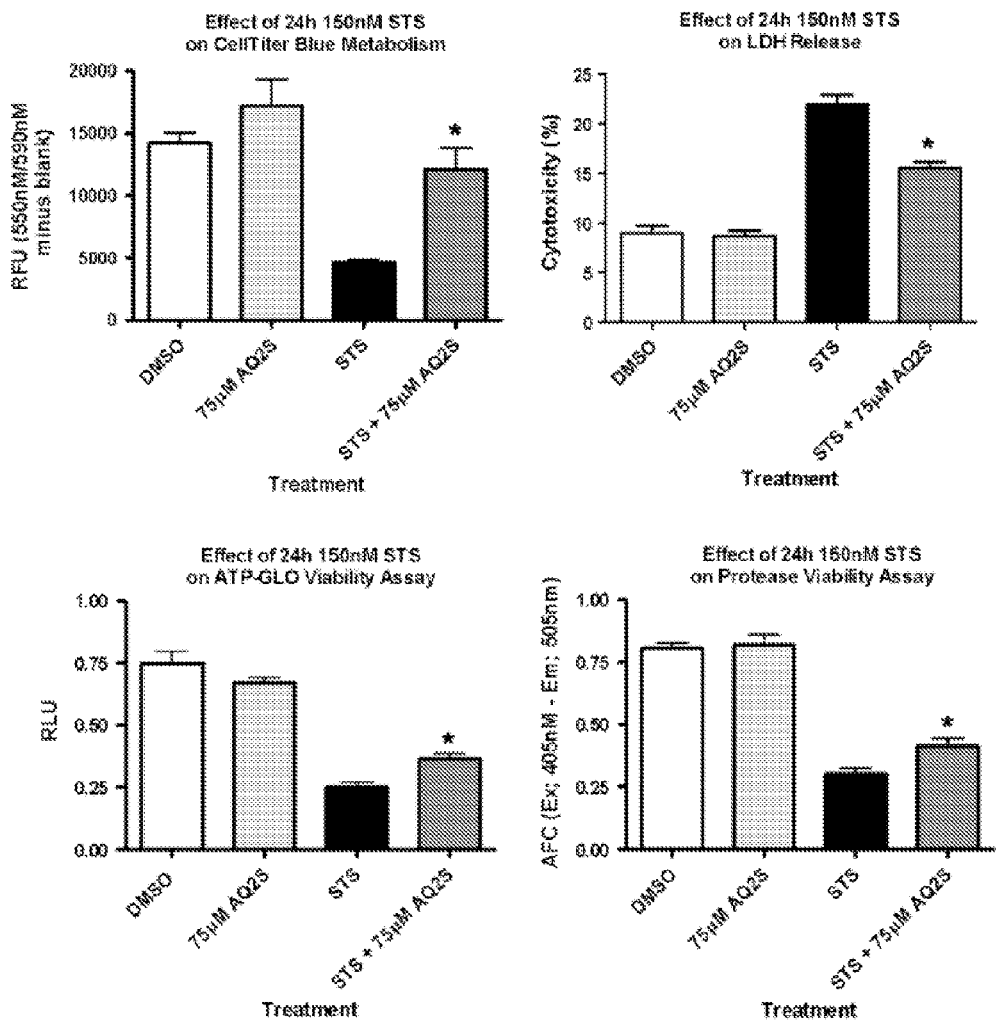
FIG. 5 is the protective effect of AQ2S against STS-induced neural death in primary rat cortical neurons validated using 4 different measures of cell survival.
Figure 6:
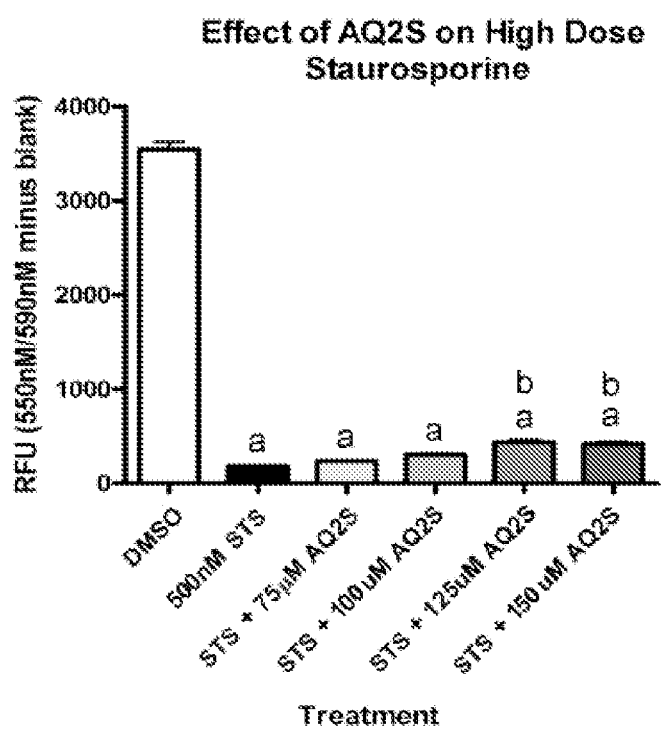
FIG. 6 is the effect of AQ2S on high doses of STS.

Co-treatment with 75 μM AQ2S significantly reduced 24 hour STS injury determined by four different assays: resazurin metabolism (CellTiter Blue; FIG. 5a), LDH release (FIG. 5b), cellular ATP levels (GLO-Viability Assay; FIG. 5c), and live-cell protease activity (CellTiter-Fluor; FIG. 5d). AQ2S alone did not significantly alter baseline viability or cytotoxicity. Studies in primary sympathetic neurons show that lower concentrations of STS induce caspase-dependent cell death, while high STS concentrations induce caspase-independent cell death mechanisms. AQ2S was tested to see if it could prevent neuronal death induced by using high dose STS. Incubation with 500 nM STS for 24 hours resulted in near total death of neurons. Co-treatment with AQ2S significantly (but only slightly) increased neuronal viability at 125 μM and 150 μM (FIG. 6).

AQ2S is a novel caspase-3 inhibitor. To further authenticate AQ2S as a novel neuroprotective compound, cultured cortical neurons were challenged with STS. Incubation of cortical neurons with 250 nM STS for 24 h significantly induced cell death (FIG. 7A; 81.1% decrease in neuronal viability), and robustly upregulated caspase3/7 activity (FIG. 7B). STS injury was repeated in the absence or presence of AQ2S. Similar to prior results, 250 nM STS reduced viability by 71.5% after 24 hours. Co-treatment with either 75 or 125 μM AQ2S significantly reduced cell death (FIG. 8A). AQ2S-treated neurons showed a 17.6% reduction in viability, compared with non-injured controls, after 24 hours STS. Moreover, AQ2S completely blocked STS-induced caspase-3 activation, and inhibited caspase-3 activity below baseline levels (FIG. 8C). Both AQ2S and Emodin were evaluated on an in vitro caspase-3 inhibitor drug screening assay. Only AQ2S and ZVAD-fmk significantly reduced the activity of recombinant caspase-3 (FIG. 8B).

Caspase-3 inhibition was confirmed by biochemical analysis. Protein samples harvested from neurons incubated with 125 μM AQ25 and 500 nM STS for 6 hours were run on western blot. Consistent with caspase-3 inhibition, cleaved (i.e., activated) capase-3 was reduced in AQ2S-treated neurons (FIG. 8D). Finally, the inhibition of caspase-3 by AQ2S was confirmed biochemically via western blot analysis of substrate cleavage products. Poly ADP ribose polymerase is a classic caspase-3 substrate. The parent protein migrates at ~116 KDa on SDS-PAGE. An 89-KDa product is produced upon cleavage by caspase-3. Cortical neurons were subjected to 250 nM STS for 6 hours. 125 μM AQ2S significantly reduced the formation of the 89-KDa species (FIG. 8E-F). In addition, protein levels of the target caspase-3 substrate NF-κB p65 subunit was increased in neurons treated with 125 μM AQ25 and 250 nM STS for 17 hours (confirming caspase inhibition). No change in the NF-κB p50 subunit was observed with injury or AQ2S treatment (FIG. 9).

Figure 10:
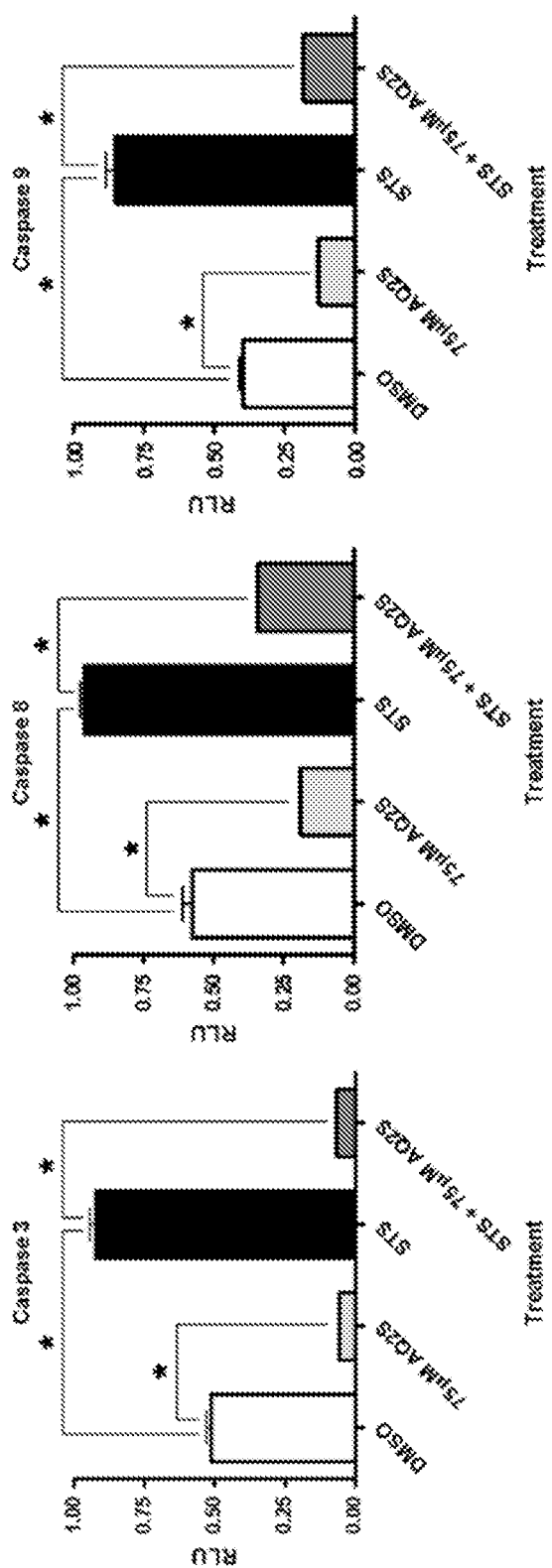
FIG. 10 is the inhibition of initiator and executioner caspases by AQ2S in primary rat cortical neurons.

Next the effect of AQ2S on other caspases was evaluated. Incubation of cortical neurons with 150 nM STS significantly increased caspase-3, caspase-8, and caspase-9 activity at 24 hours. Co-treatment with 75 μM AQ2S significantly reduced baseline and injury activity levels of all three caspases (FIG. 10). However, 75 μM AQ2S showed greatest potency against caspase-3.

AQ2S does not Interfere with the Luciferase Reaction. The in vitro caspase 3, 8, and 9 activity assays (Promega, Madison, Wis., USA) utilize luminescence as a proxy for enzyme activity. Luminescent assays are commonly used in drug discovery to screen compounds for biological action (e.g. caspase inhibitors). Although a powerful technique, the inhibition of luciferase signal by chemical interference (false-positive) remains a significant problem. Artifact-dependent inhibition of luminescent signal occurs via 3 primary mechanisms. 1) Redox cycling of a chemical interferes with the oxidation of luciferin substrate. 2) Production of reactive radical species by redox active chemicals destroys the luciferase enzyme. 3) Colored/fluorescent compounds interfere with luciferase signal detection by a luminometer.

AQ2S is used in photochemistry, under non-physiological conditions, to study the redox cycling behavior of anthraquinones. In addition, dissolved in DMSO, AQ2S presents a faint yellow hue. To test if AQ2S mediated inhibition of caspase3/7 was artifact, the effect of different AQ2S concentrations on 2 different cell viability tests were compared (one test fluorometric and the other luminescent). AQ2S was incubated at the indicated concentrations for 24 hours. After 24 hours, the cell viability reagent was added and cell survival assayed. As measured by the fluorometric CellTiter Blue assay, none of the AQ2S concentrations used inhibited viability below control levels (FIG. 11A). Similar results were observed using the luminescent viability-GLO assay (FIG. 11B). Finally, to replicate the exact experimental conditions used in injury studies, neurons were first incubated with the CellTiter Blue reagent for 2 hours. Subsequently, the viability-GLO reagent was added for 1 hour and luminescence measured (i.e. viability reagents were mixed together; FIG. 11C). When both assays were combined, AQ2S caused a ~13-17% decrease in luminescent signal compared to DMSO controls. The data support that AQ2S is a novel caspase inhibitor.

AQ2S Activates the Pro-Survival Kinase AKT. AKT is a key pro-survival kinase that is dysregulated by acute brain injury. Many diverse therapies used to prevent neuronal death activate AKT, including small molecules, endogenously derived survival proteins, and other non-pharmacology based treatments like therapeutic hypothermia. To further elucidate the mechanisms of AQ2S-mediated neuroprotection, the level of activated (phosphorylated) AKT was measured by western blot.

Figure 12:
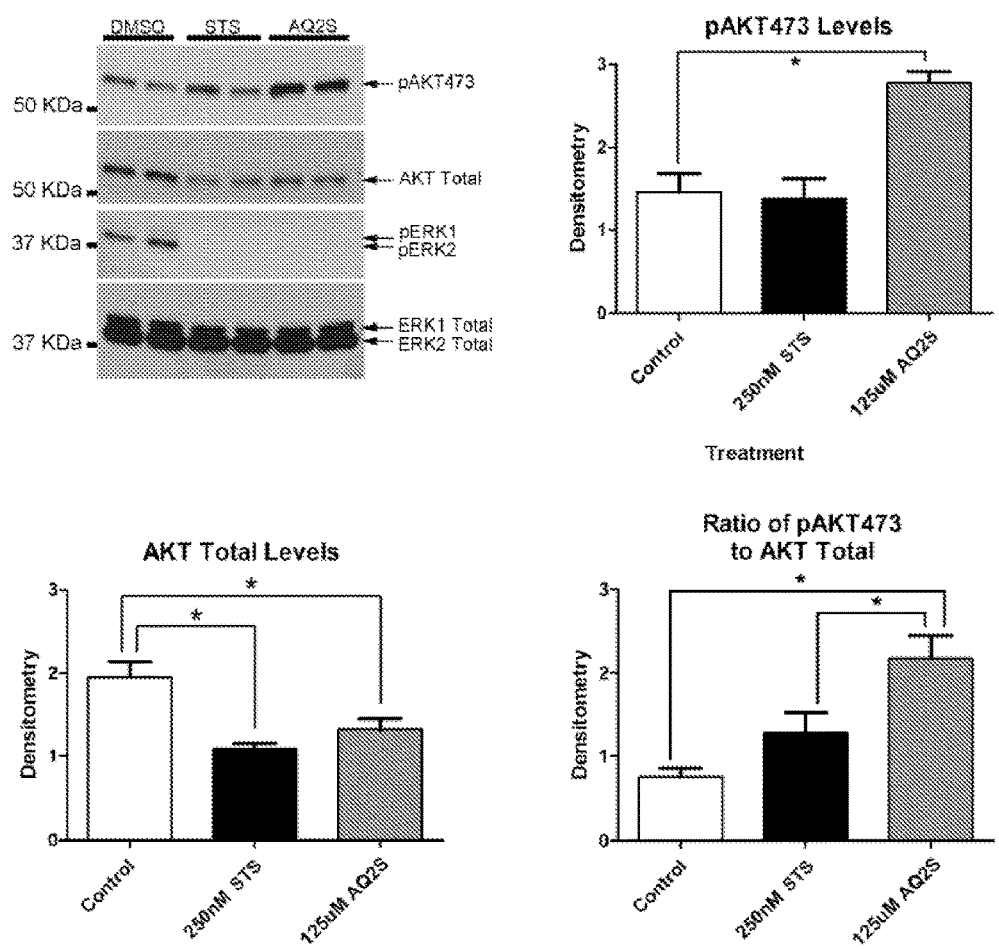
FIG. 12 is the activation of AKT by AQ2S after long-term STS exposure.

Consistent with the neuroprotective profile of AQ2S, only neurons co-treated with 125 µM AQ2S showed a significant elevation in AKT activity (pAKT473) after 17 hours STS injury (FIGS. 12A and 7B). However, total AKT levels were significantly reduced in all STS treated groups (FIGS. 12A and 12C). Therefore, compared to non-injured controls, the ratio of pAKT473/AKT was slightly elevated after STS injury (though not significant) but highest in the AQ2S treated group (FIG. 12D). To determine the specificity of AQ2S mediated signaling changes, extracellular regulated kinase (ERK) was also examined. 17 hours STS abolished ERK activation. AQ2S treatment did not prevent STS-mediated ERK inhibition. Moreover, total ERK levels did not change (FIG. 12A).

AQ2S-mediated AKT activation was first assayed under non-injury conditions. 125 µM AQ2S was added to fresh neurobasal/B27 media and incubated for 4 and 24 hours. AQ2S induced a significant (but modest) rise in pAKT473 after 4-hours treatment (FIG. 13a, c and e). No effect on AKT total was observed (FIG. 13d). Alternatively, the effect of AQ2S on pAKT473 was not significant at 24 hours (FIG. 13b).

AQ2S was also tested to see if it increased pAKT473 after STS injury. We compared the effects of AQ2S and emodin to modulate pAKT473 after 6 hours at 250 nM STS. STS alone induced AKT activation. AQ2S marginally increased STS-induced pAKT473 at the 6-hour time point, but did not reach statistical significance. Alternatively, 50 µM emodin abolished baseline and injury induced AKT activation (FIGS. 14a and b).

To determine if AKT activation is critical for AQ2S-mediated neuroprotection, neurons were injured with 250 nM STS in the absence or presence of 125 µM AQ25 and 10 µM LY294002 (PI3K/AKT inhibitor) for 21 hours. Consistent with previous observations, pAKT473 and pERK levels were decreased by STS injury. In addition, pAKT473 increased in the presence of AQ2S, and AQ2S-induced pAKT473 was blocked by LY294002 (FIG. 15a). However, after 24 hours 250 nM STS injury, LY294002 failed to block AQ2S-mediated neuroprotection (FIG. 15b).

Figure 16:
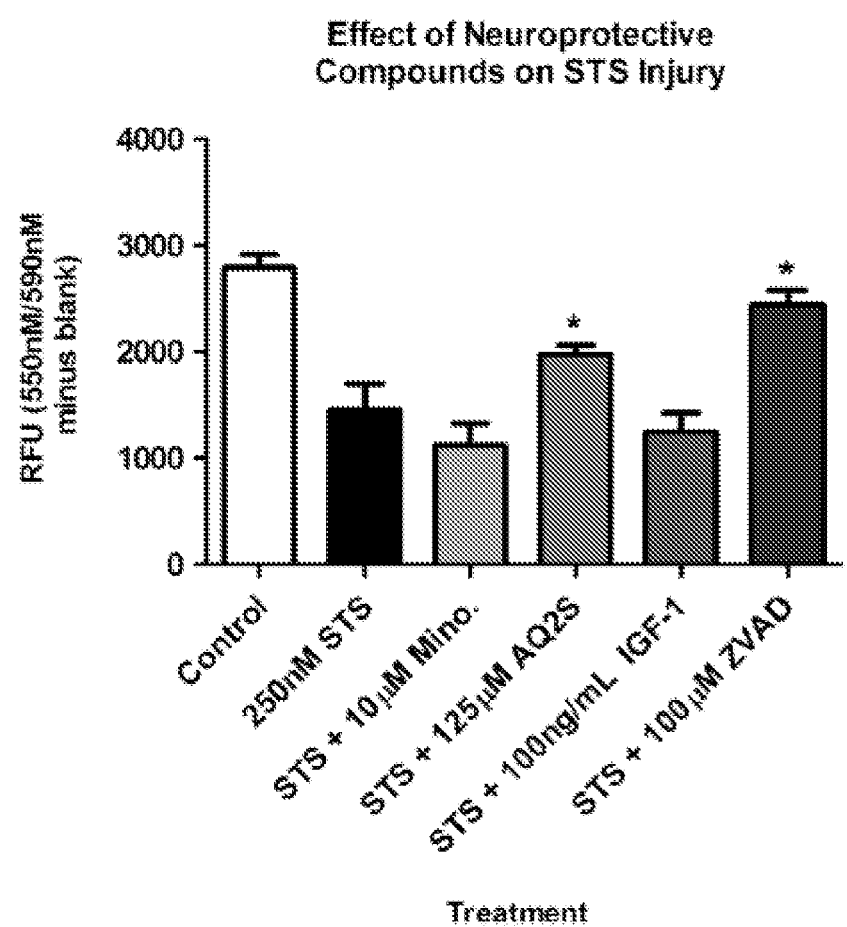
FIG. 16 is the comparison of AQ2S to other known neuroprotectants against STS injury in primary rat cortical neurons.

Finally, we compared the protective effect of AQ2S to other documented neuroprotectants. 250 nM STS was co-administered with minocyline, AQ2S, IGF-1 or ZVAD for 24 hours. Only ZVAD and AQ2S increased cell viability after 24 hours (FIG. 16). Neither minocycline nor IGF-1 reduced neuronal death. However, 24 hours of IGF-1 pre-treatment is neuroprotective and reduces a subsequent 24 hour STS injury.

AQ2S does not Promote Lipid Peroxidation. Identifying harmful biological side effects of novel small-molecule drugs is a critical component of pharmacotherapeutics. Many quinone species are toxic redox cycling chemicals, and increase the level of reactive radicals. In turn, reactive radicals promote lipid peroxidation and cause cellular damage. Germane to the study of AQ2S, clinical evidence indicates that some anthraquinone based drugs increase lipid peroxidation, and is a significant safety concern when using these compounds.

Figure 17:
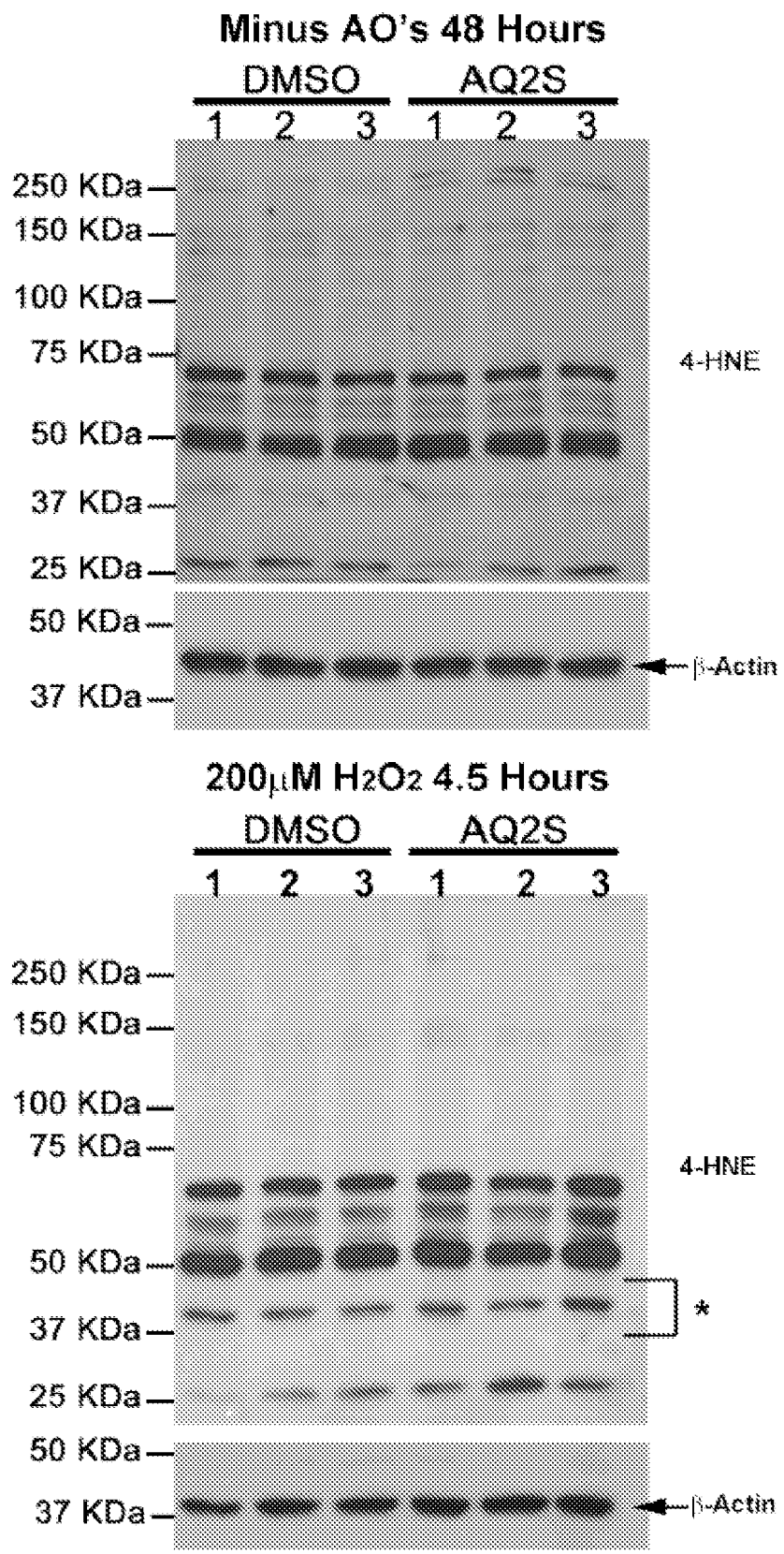
FIG. 17 is the non-promotion of lipid peroxidation by AQ2S in uninjured and during oxidative stress of primary rat cortical neurons.

To test if AQ2S promotes lipid peroxidation in neurons, at D.I.V. 12, culture media was exchanged with Neurobasal/B27 (-AO) in the absence or presence of 125 µM AQ2S for 48 hours. D.I.V. 14 neurons were harvested and analyzed for 4-HNE levels. AQ2S did not significantly increase the basal level of 4-HNE (unpaired t-test, P=0.1856; FIG. 17a).

Injury (e.g. brain ischemia), robustly increases endogenous reactive oxygen species (ROS) levels. ROS may promote the formation of deleterious quinone radicals and increase lipid peroxidation. The potential enhancement by AQ2S of lipid peroxidation induced by 200 µM $H_2O_2$ was evaluated. D.I.V. 13 neurons were treated for 4.5 hours with 200 µM $H_2O_2$ in fresh neurobasal/B27 (-AO) in the presence or absence of 125 µM AQ2S. 200 µM $H_2O_2$ increased 4-HNE levels. The asterisk in FIG. 17b indicates an approximate 40-45 KDa band, particularly, sensitive to treatment. AQ2S did not significantly up-regulate 4-HNE staining after a 4.5-hours incubation (unpaired t-test; P=0.0901; FIG. 17b).

Recent studies indicate that natural anthraquinones prevent neuronal death. Contrary to these studies, emodin, rhein, and aloin are not neuroprotective when administered after $H_2O_2$ injury.

Preconditioning neurons with non-lethal doses of toxins or ROS activators is neuroprotective. 50 µM emodin increases ROS and induces cell death of lung adenocarcinoma cells. Moreover emodin increases ROS and caspase activation in microglia derived BV-2 cells. It was found that 1) postinjury treatment with low dose emodin is not protective, and 2) 50 µM emodin exacerbates injury. The data presented herein suggest that emodin is a mild toxin. Consistent with this idea, prior work indicates that emodin therapy upregulates antioxidant defenses. Preconditioning may explain, in part, previously reported emodin induced neuroprotection for $H_2O_2$ injury.

Figure 2:
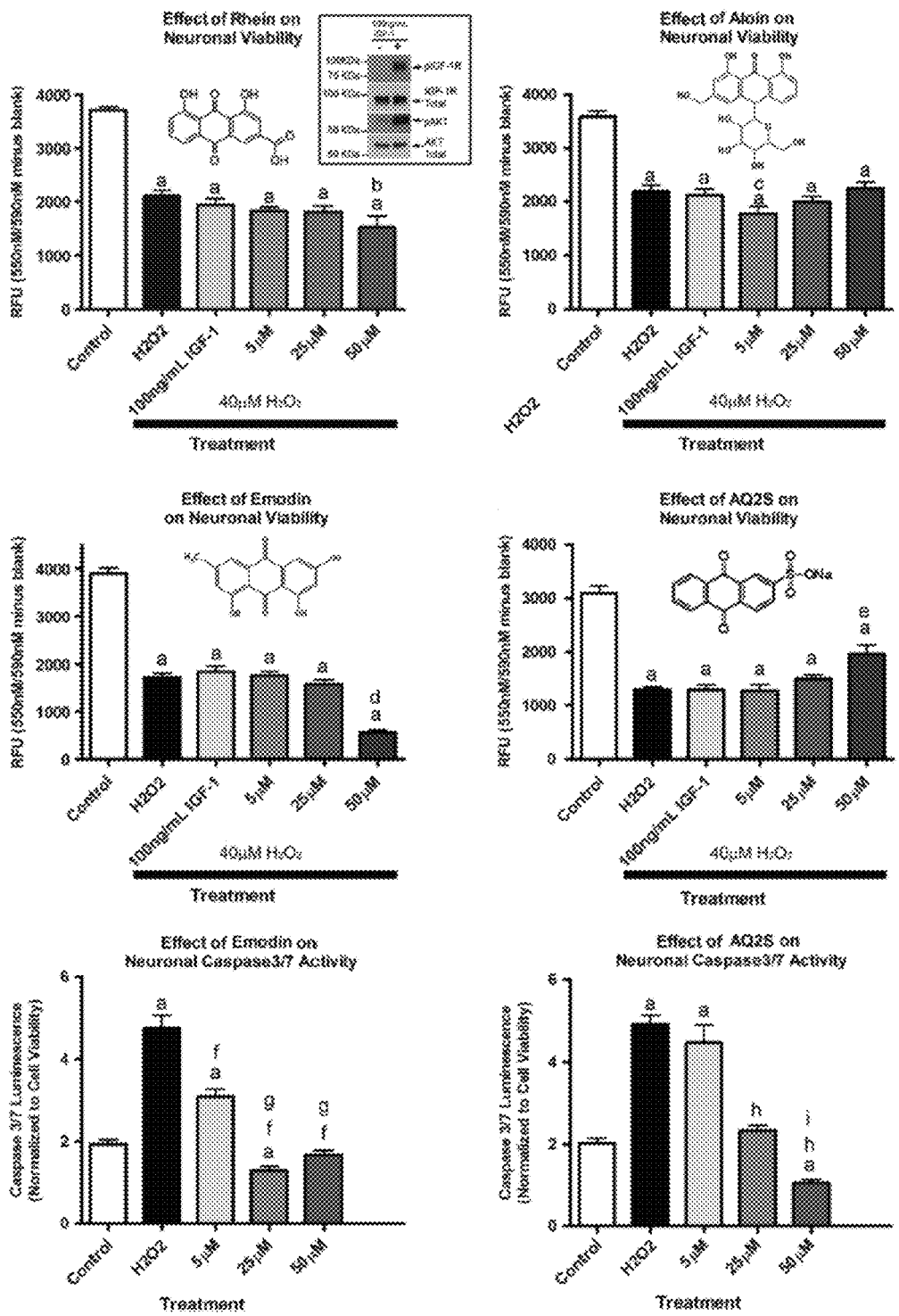
FIG. 2 is the effect of anthraquinones on $H_2O_2$ injury on primary rat cortical neurons.
Figure 8:
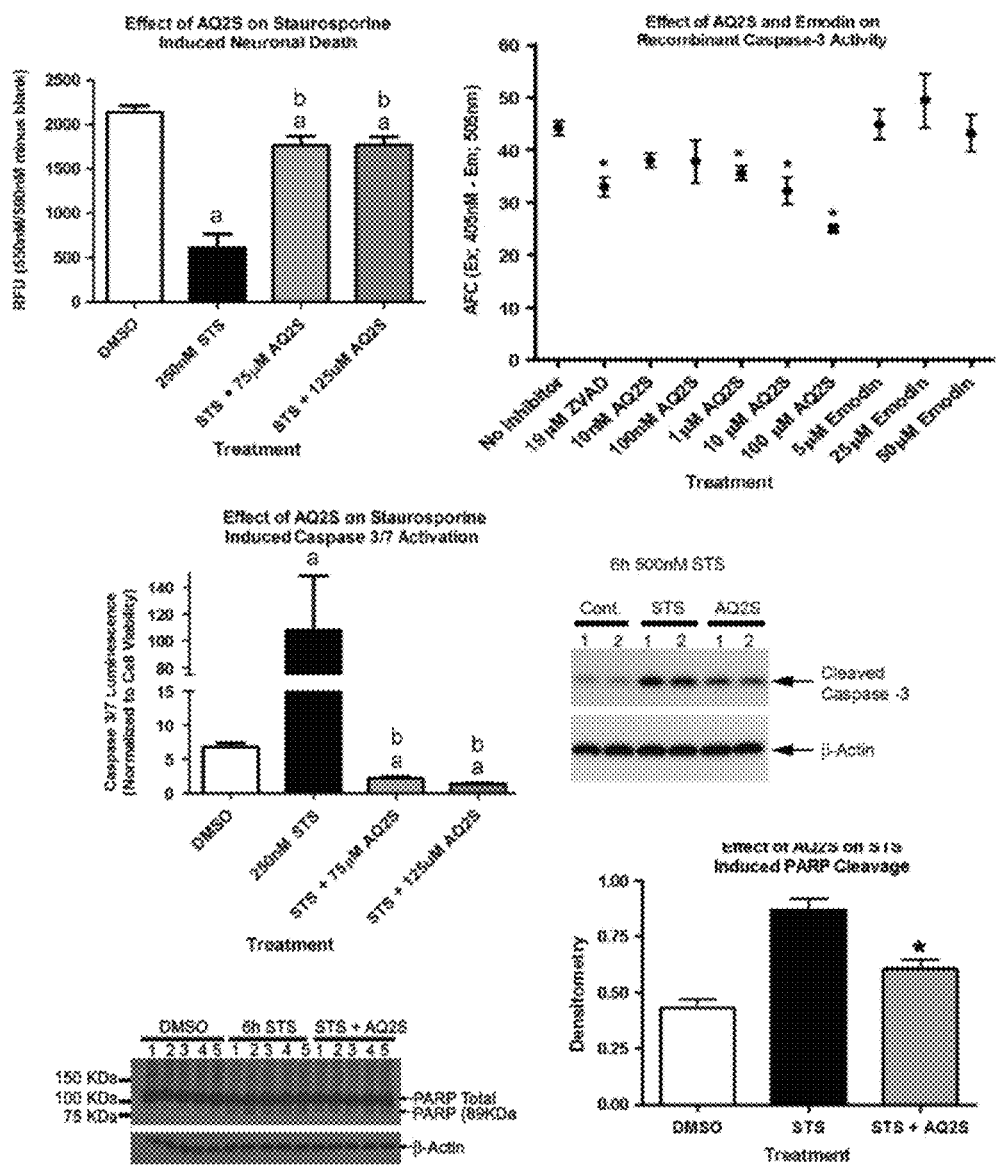
FIG. 8 is the direct caspase-3 inhibitory activity of AQ2S in an in vitro cell-free assay, and caspase-3 regulated biochemistry measured in primary rat cortical neurons.
Figure 9:
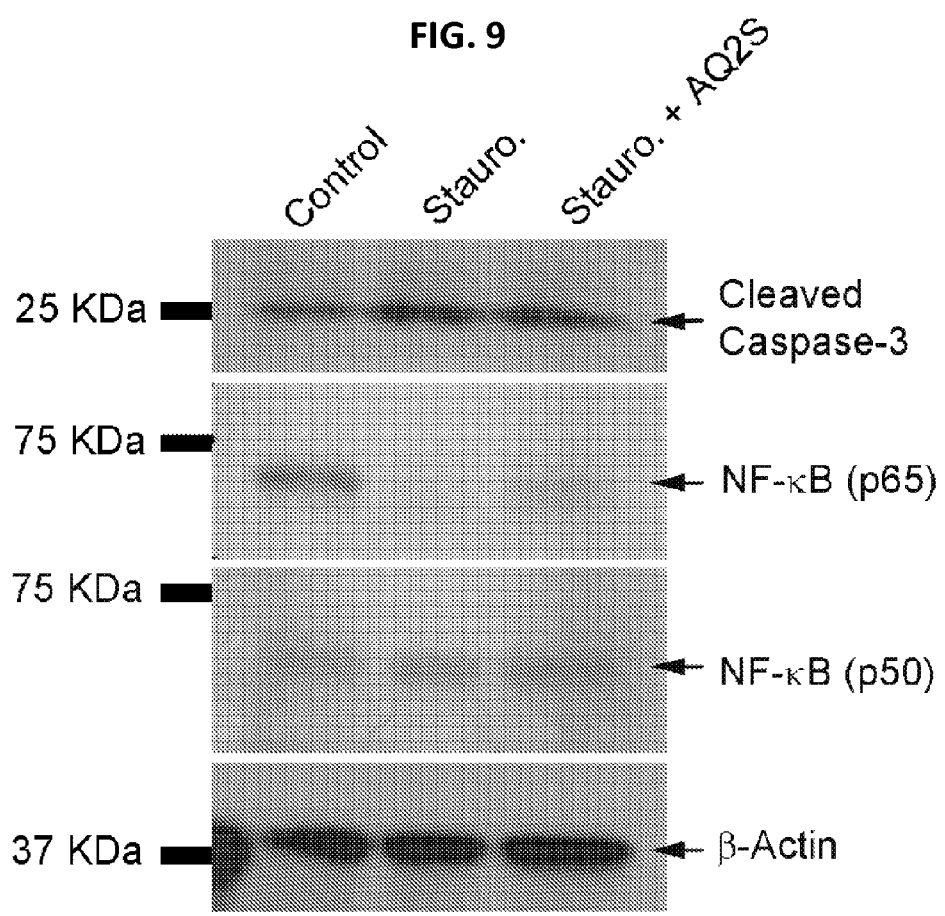
FIG. 9 is the inhibition of caspase-3 cleavage of NF-κB by AQ2S.

FIG. 2 shows that emodin reduced caspase-3 activity in neurons but it was not a direct caspase inhibitor in the cell-free assay (FIG. 8). Studies show that high $H_2O_2$ concentrations can inhibit caspase-3 activation. 24 hour emodin may have exacerbated oxidative stress in this system and inhibited caspase-3 by indirect mechanisms (explaining the discrepancy in FIGS. 2 and 8). Caspase-3 inhibition via oxidative mechanisms would not prevent necrosis. Moreover, 50 µM emodin may have potentiated cell death by reducing AKT473 levels in cortical neurons; synergizing with $H_2O_2$-induced impairment of IGF-1/AKT survival signaling.

AQ2S is a non-toxic quinone with unique redox properties. AQ2S is a synthetic anthraquinone used in wood pulping, and the basis for many anthraquinone dyes. Given the focus on industrial utilities, not surprisingly, few studies have examined AQ2S in biological systems. From the available sources, it was predicted that AQ2S would behave as a toxic agent and emodin would exert neuroprotective actions. Unexpectedly, the opposite was achieved. Not only was AQ2S safe, it protected neurons from oxidative and chemical injury. This is the first time that AQ2S has been shown to prevent cellular injury. However, in the context of this novel observation that AQ2S is neuroprotective, prior work may help explain the lack of toxicity.

A primary danger of quinone compounds in biological systems is that highly reactive by-products/intermediates are produced from their metabolic biotransformation. Bayol-Denizot et al. investigated the metabolism of AQ2S by NADPH-cytochrome P450 reductase in primary rat neurons, astrocytes, and cerebral endothelial cells. In vitro incubation of 980 µM AQ2S, significantly upregulated superoxide anion ($O_2.^-$) levels in all 3 cell types measured over a 60 minute period. However, the author's note a lack of toxicity at 980 µM AQ2S. At very high concentrations AQ2S was toxic (cell viability rapidly decreased to 50% at 5000 µM). Importantly, the authors also found that the AQ2S induced $O_2.^-$ was blocked by increasing concentrations of SOD. Alternatively, SOD was incapable of fully blocking $O_2.^-$ produced by menadione, another xenobiotic under study. The findings indicate that the redox chemistry of AQ2S is unique compared to other xenobiotics.

There have been reports on the unique redox behavior of AQ2S compared to other quinones. Winterbourn examined the ability of semiquinone radicals to reduce cytochrome c under artificial conditions. Moreover, the effect of SOD to inhibit quinone radical formation, in the presence of molecular oxygen ($O_2$) was explored. All quinones tested, including AQ2S radicals, reduced cytochrome c. However, only AQ2S-mediated cytochrome c reduction (but not menadione, benzequinone, and several other napthroquinones) was fully blocked by addition of SOD. Winterbourn hypothesized that AQ2S prefers the oxidized (non-radical) state because of its negative redox potential (AQ2S; $E°=-0.39$). AQ2S has a redox potential that is lower than oxygen ($O_2$; $E°=-0.17$), and lower than the other quinones tested. In the presence of $O_2$, AQ2S is a less attractive electron acceptor. Therefore, the majority of electrons remain with $O_2$ to form $O_2.^-$ radicals (which are rapidly eliminated by SOD, preventing cytochrome c reduction). Consistent with these reports, we observe little effect of AQ2S to inhibit luminescence signal by redox artifacts; indicating that either AQ2S is a relatively mild redox agent or radical production can be managed by endogenous scavenging mechanisms.

The redox chemistry of a drug has important clinical implications. ROS can lead to toxic lipid peroxidation. For example, Doxorubicin (DOX) is an anthraquinone based chemotherapeutic agent. The primary limitation of DOX therapy for the treatment of cancer is cardiotoxicity due to lipid peroxidation. Radical formation-mediated lipid peroxidation is a shared trait amongst many quinone species. Vile and Winterbourn compared the ability of different quinones to generate quinone radicals and reduce iron ($Fe^{3+}$) in rat liver microsomes; the reduction of $Fe^{3+}$ plays a key role in lipid peroxidation. Despite significant increases in AQ2S mediated $Fe^{3+}$ reduction (which should have increased lipid peroxidation), AQ2S actually inhibited microsomal lipid peroxidation (as measured by significant reductions in the formation of thio-barbituric acid reactive products). The authors lacked a mechanistic explanation for the counterintuitive observation but suggest AQ2S may interfere with redox processes downstream of $Fe^{3+}$ reduction. Similarly, Huang et al. showed that emodin and alizarin (an AQ2S derived anthraquinone dye) inhibit lipid peroxidation in rat heart mitochondria. Both compounds reduce lipid peroxidation but utilize different mechanisms. Alizarin was a free radical scavenger while emodin was not.

In the present study AQ2S did not raise 4-HNE levels. The absence of increased lipid peroxidation suggests that AQ2S may be a safe/well tolerated anthraquinone drug. Consistent with this idea, as indicated by the Registry of Toxic Effects of Chemical Substances (RTECS database) AQ2S (ID: CB1095550) has a relatively high intraperitoneal Acute $LD_{50}$ in mice (630 mg/kg) and rats (730 mg/kg). Moreover, the National Cancer Institute (NCI), Drug Evaluation Branch, Research and Development Division of Cancer Treatment, has for over 30 years tested novel chemicals for anti-cancer potential using in vivo models (results are assessable via NCI's Development Therapeutics Program website; http://dtp.nci.nih.gov/webdata.html). Curiously, AQ2S(NCI ID: NCS229389) was screened for possible antitumor activity in mice. AQ2S was administered to mice via IP injections of either 100 mg/kg, 200 mg/kg, or 400 mg/kg. Although AQ2S did not inhibit tumor formation, all animals survived to toxicology day 5 (indicating that high concentrations of AQ2S were well tolerated in vivo). To the best of our knowledge this is the only report of AQ2S being tested as a disease modifying agent.

AQ2S-mediated mechanism(s) of neuroprotection. AQ2S does not behave like a toxic agent. Moreover, despite the intention to use AQ2S as a negative control, it alone induced neuroprotection in both the $H_2O_2$ and STS injury assay. To understand the mechanisms of neuroprotection, caspase 3/7 activity was analyzed first. AQ2S behaved as a powerful caspase inhibitor in both injury models. AQ2S blocked caspase activation after injury, and reduced caspase levels below baseline non-injured levels. Emodin also inhibited caspase activity on the $H_2O_2$ assay but was not neuroprotective. One explanation is that caspase inhibition alone is insufficient to prevent $H_2O_2$ mediated cell death. Moore et al. examined the neuroprotective effect of the pan-caspase inhibitor BAF on primary rat cortical neurons that were injured by 24 hour 500 nM STS, 50 µM C2-ceramide, 10 µM camptothecin, 50 µM $H_2O_2$ and 100 µM N-methyl-D-aspartic acid (NDMA). Caspases were activated in all but the NMDA assay. Moreover, BAF reduced cell death in every model where caspase was activated except $H_2O_2$. The finding suggests that caspase inhibition is insufficient to induce neuroprotection after $H_2O_2$ injury. Therefore, AQ2S may activate both caspase-dependent and -independent survival mechanisms.

AQ2S barely induced neuroprotection under high STS (500 nM) conditions, however, robustly prevented cell death if co-treated with 250 nM STS. Deshmukh and Johnson, using in vitro primary rat sympathetic neurons, report that low concentrations of STS (100 nM) for 48 hours induce caspase-dependent cell death, while high STS concentrations for 48 hours (500 nM and 1000 nM) induce caspase-independent cell death. BAF prevented neuronal death at the 100 nM STS concentration but failed to prevent cell death at the 500 nM and 1000 nM concentrations. More strikingly, the authors found that 4 out of 9 cell death assays resulted in false-negatives when used to measure cell viability at the 500 nM and 1000 nM STS doses. The authors suggest that the failure of some assays to detect cell death is related to high dose STS inhibiting proteins involved in cellular degradation (creating a form of "cellular mummification;" clear evidence of a divergence in the form of cell death that results from low dose and high dose STS). Nevertheless, in the present assay, AQ2S likely blocked caspase-dependent cell death mechanisms (operating at the 250 nM STS dose) but was unable to inhibit alternative cell death mechanisms activated by 500 nM STS.

Figure 13:
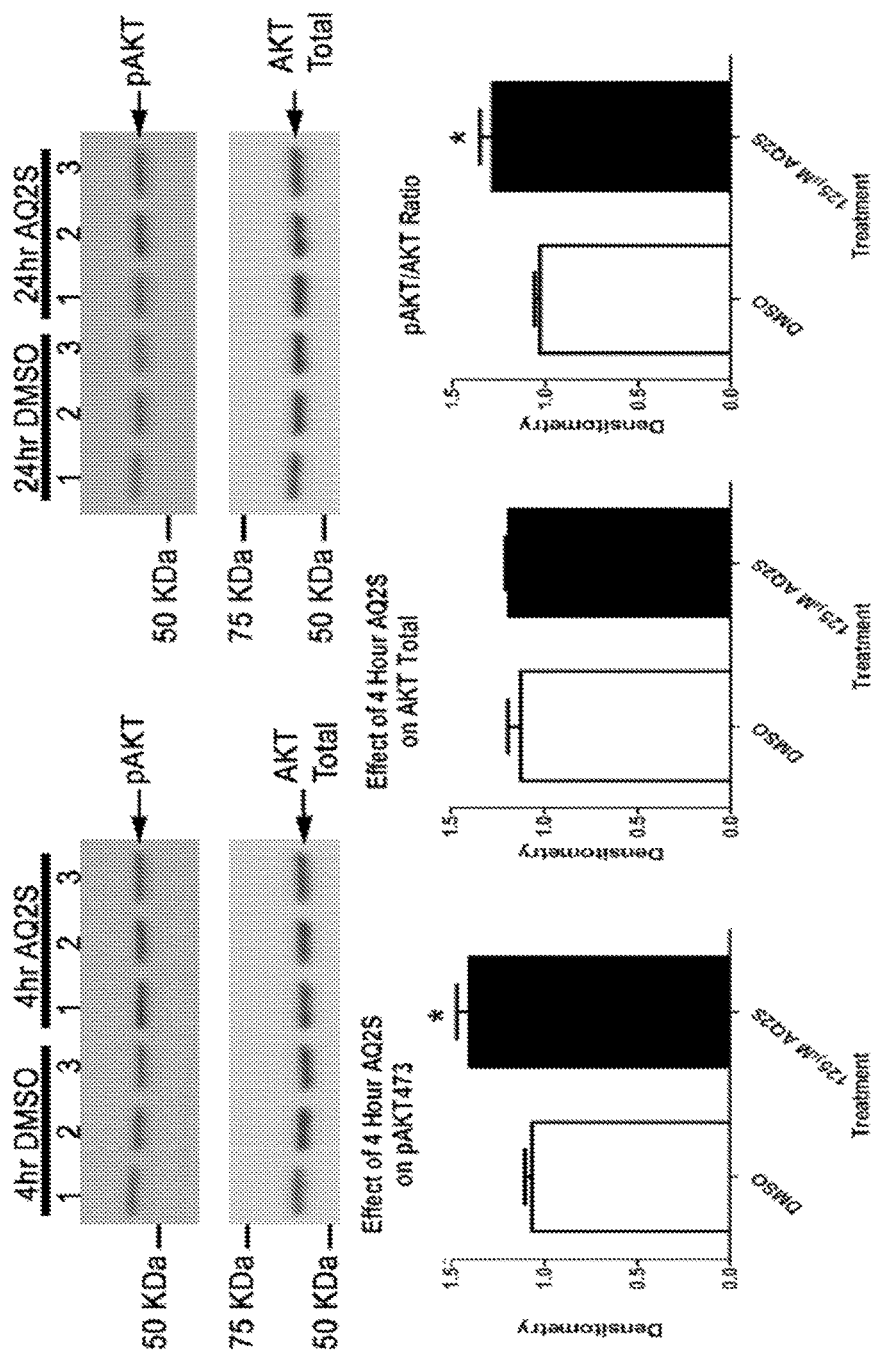
FIG. 13 is the activation of AKT by AQ2S under baseline conditions, measured in primary rat cortical neurons.

To further characterize the neuroprotective actions of AQ2S the induction of the pro-survival kinase AKT by drug treatment was evaluated. It was observed that AQ2S potently stimulates AKT activity under injury conditions (at 17 hours, FIGS. 12 and 21 hours, FIG. 15) but only moderately activates AKT under non-injury conditions (FIG. 13). Unexpectedly however, preventing AKT activation with LY294002 failed to block AQ2S's neuroprotective action in the STS injury assay (FIG. 15). A simple explanation is that caspase inhibition is enough to achieve neuroprotection after STS injury. Alternatively, AKT activation may play a more important role in other injury paradigms such as $H_2O_2$. However, previous work shows that overexpression of constitutively active AKT prevents STS induced cell death in a dorsal root ganglion cell line. Therefore AKT activation plays a role in survival signaling in the STS injury model as well, indicating that AQ2S is activating multiple survival mechanisms.

Finally, AQ2S may work by targeting alternative neuroprotective pathways. For example, studies indicate that certain synthetic anthraquinones (e.g. 2-aminoanthraquinone) can act as NMDA channel blockers. However, AQ2S lacks an amino group. The amino group was essential to achieve NMDA receptor inhibition in the previous anthraquinone studies (interacts with key residues in the protein). Thus it is unclear if AQ2S can target this mechanism.

AQ2S is a RBM Inhibitor. A more exciting possibility is that AQ2S targets an entirely unexplored and novel neuroprotective pathway. RNA binding motif 5 (RBM5) is involved in mRNA splicing of pro-apoptotic genes. The zinc finger domain found within RBM5 allows it to bind to target pre-mRNA sequences. During pre-mRNA processing, RBM5 regulates the inclusion or exclusion of specific exons into the final mature mRNA sequence (i.e. it regulates splice variation of target proteins). Importantly, RBM5 activation upregulates the pro-apoptotic splice variant versions of many cell death proteins, and its inhibition upregulates the anti-apoptotic versions. A prototypical example is regulation of caspase-2. The classic pro-apoptotic protein is caspase-2L. The anti-apoptotic splice variant is caspase-2S. RBM5 prevents inclusion of exon 9 into the final caspase-2 mRNA which promotes the pro-death caspase-2L variant.

A recent study found that AQ2S is the world's first selective RBM5 inhibitor (though it may also target other related RBM's). To the best of our knowledge no study has ever tested if RBM5 plays a role in neuronal cell death or brain injury. Intriguingly, the $IC_{50}$ of AQ2S to inhibit RBM5 was ~82 µM. Maximal protection was observed at 75-125 µM AQ2S. This suggests that inhibition of RBM5 may be an important neuroprotective mechanism. Therefore, the results presented herein are the first to show a role for RBM5 in neuronal injury.

In summary, presented herein is evidence that the synthetic anthraquinone AQ2S potently prevents death of primary neurons. This work indicates that AQ2S is a lead compound to develop a novel class of neurotherapeutic drug. This has important implications for the treatment of traumatic brain injury (TBI), stroke, and cardiac arrest (CA). In addition, AQ2S therapy may help to prevent neurodegenerative pathologies such as Alzheimer's. Future studies need to further elucidate the mechanisms of action, test if AQ2S is neuroprotective in clinically relevant in vivo brain injury paradigms, and manipulate the core structure to optimize blood brain barrier (BBB) penetration and bioavailability. In addition, the anthraquinones are able to treat non-CNS injuries, such as heart ischemia and kidney ischemia.

The following statements point out particular aspects for explanatory purposes.

1. A method of treating or preventing brain injury or disease by administering a sulfonated anthraquinone.

2. The method of statement 1 wherein said anthraquinone is anthraquinone-2-sulfonic acid.

3. The method of statement 1 wherein said anthraquinone is a pro-drug of anthraquinone-2-sulfonic acid.

4. The method of statement 1 wherein said anthraquinone is any salt form or analog of anthraquinone-2-sulfonic acid.

5. The method of statement 1 wherein a sulfonated anthraquinone is formulated for oral, intravenous, intranasal, or inhalation routes of administration.

6. The method of statement 1 wherein a sulfonated anthraquinone is administered alone, or in combination with standard of care therapies including therapeutic hypothermia.

7. The method of statement 1 wherein the injury is an acute brain injury.

8. The method of statement 7 for the treatment of traumatic brain injury (TBI).

9. The method of statement 7 for the treatment of ischemic brain injury by cardiac arrest (CA).

10. The method of statement 7 for the treatment of ischemic brain injury by stroke, hemorrhage, or contusion.

11. The method of statement 1 for the treatment of Alzheimer's disease.

12. The method of statement 1 for the treatment of Parkinson's disease.

13. The method of statement 1 for the treatment of Huntington's disease.

14. The method of statement 1 for the treatment of metabolic diseases affecting brain function and health.

15. A method of treating or preventing brain injury or disease by administering an RBM inhibitor.

16. The method of statement 15 wherein said RBM inhibitor is anthraquinone-2-sulfonic acid.

17. The method of statement 15 wherein said RBM inhibitor is a pro-drug of anthraquinone-2-sulfonic acid.

18. The method of statement 15 wherein said RBM inhibitor is any salt form or analog of anthraquinone-2-sulfonic acid.

19. The method of statement 15 wherein said RBM inhibitor is formulated for oral, intravenous, intranasal, or inhalation routes of administration.

20. The method of statement 15 wherein said RBM inhibitor is administered alone, or in combination with standard of care therapies including therapeutic hypothermia.

21. The method of statement 15 wherein said RBM inhibitor is a small molecule drug, siRNA/shRNA, antisense sequence, or antibody.

22. The method of statement 15 wherein said RBM inhibitor targets one or multiple pro-apoptotic RBM proteins in any combination.

23. The method of statement 22 wherein target protein is RBM5.

24. The method of statement 22 wherein target proteins are RBM4, RBM6, RBM10 and/or RBM11.

25. The method of statement 15 wherein the injury is an acute brain injury.

26. The method of statement 25 for the treatment of traumatic brain injury (TBI).

27. The method of statement 25 for the treatment of ischemic brain injury by cardiac arrest (CA).

28. The method of statement 25 for the treatment of ischemic brain injury by stroke, hemorrhage, or contusion.

29. The method of statement 15 for the treatment of Alzheimer's disease.

30. The method of statement 15 for the treatment of Parkinson's disease.

31. The method of statement 15 for the treatment of Huntington's disease.

32. The method of statement 15 for the treatment of metabolic diseases affecting brain function and health.

Further Examples

Neuronal Cell Culture.

Cultures were maintained using our previously published techniques that yield an enriched neuron population (95% neurons). Briefly, brains were isolated from E18-19 sprague dawley rat embryos. Embryonic cortical brain tissue was bathed in cold dissection solution (hanks balanced salt solution, HBSS; sodium bicarbonate; HEPES; penicillin/ streptomycin) and isolated under a dissecting microscope (Leica M651). Roughly 8-10 brains (16-20 cortical halves) were collected in a 1.5 mL centrifuge tube and rapidly minced over a 2 minute period using sterile scissors. Tissue was spun at 4° C./200 g/5 minutes and supernatant discarded. Tissue pellet was resuspended in trypsinization solution and gently rocked in a water bath for 8 minutes. Trypsin was quenched is neurobasal/B27 with 5% heat inactivated fetal bovine serum, and spun at 4° C./200 g/5 minutes. Supernatant was discarded and cell pellet resuspended in trituration solution. Neurons were further dissociated in trituration media via a fire polished glass pipette. Neurons were given a final spin at 4° C./200 g/5 minutes. Supernatant was discarded and neurons were resuspended in plating media (neurobasal/B27 supplemented with 25 µM glutamic acid). Neurons were counted using a hemacytometer and plated at high density (~$1.2 \times 10^6$/well of a 6-well plate; ~$1.5 \times 10^5$/well of a 96-well plate) on poly-D-lysine coated plates (BD Biosciences). Neurons were maintained with fresh neurobasal/B27 supplemented media. Every 3 days, ½ the media was replaced with fresh neurobasal/B27. On D.I.V. 3, 8 µM cytosine β-D-arabinofuranoside hydrochloride was added to prevent glial proliferation. Experiments were performed between D.I.V. 10-14.

$H_2O_2$ Injury.

Primary rat cortical neurons were harvested and plated in neurobasal/B27 (with antioxidants; +AO). Neurons were switched to neurobasal/B27 minus antioxidants (-AO) after D.I.V. 3. Fresh media was exchanged by half-media replacement at D.I.V. 3, 6, 9. $H_2O_2$ was prepared fresh before each injury experiment. At D.I.V 10, 30% concentrated $H_2O_2$ (Sigma) was first diluted in sterile dd$H_2O$. Diluted stock $H_2O_2$ was directly added to unprepared (no B27 supplement) neurobasal media at the desired final concentration. Growth maintenance media was aspirated from neurons in 96-well format, and replaced with 150 µL neurobasal media containing $H_2O_2$ incubated for 35 minutes. Following injury, neurobasal/$H_2O_2$ media was aspirated and replaced with 100 µL fresh neurobasal/B27-AO's containing test drugs, DMSO only, or IGF-1/DMSO at desired concentrations and incubated for 24 hours. Equal concentrations of DMSO were used for all injury experiments/treatment conditions. The results are shown in FIG. 2. The effect of 100 ng/mL IGF-1 and rhein on 24 hour neuronal death is shown in FIG. 2. (a). Validation of IGF-1 stimulation is shown in the boxed western blot insert. Both IGF-1R and Akt are activated after 25 minutes stimulation with 100 ng/mL IGF-1 in 2 hour supplement starved cortical neurons. (b) The effect of 100 ng/ml IGF-1 and aloin on neuronal death. (c) The effect of 100 ng/ml IGF-1 and emodin on neuronal death. (d) The effect of 100 ng/ml IGF-1 and AQ2S on neuronal death. (e) The effect of emodin on $H_2O_2$-induced caspase 3/7 activation. (f) The effect of AQ2S on $H_2O_2$-induced caspase 3/7 activation. Horizontal black bars indicate groups treated with 40 µM $H_2O_2$. a=compared with no injury DMSO control (white bar), b=compared with injury only DMSO (black bar) and IGF-1, c=compared with injury only DMSO (black bar) and 50 µM aloin, d=compared with injury only DMSO (black bar), IGF-1, 5 emodin, and 25 µM emodin, e=compared with injury only DMSO (black bar), IGF-1, and 5 µM AQ2S, f=compared with injury only DMSO (black bar), g=compared with 5 µM emodin, h=compared with injury only DMSO (black bar), i=compared with 25 µM AQ2S. Data was analyzed using one-way-ANOVA (n=8/ treatment; P<0.0001; graphs show mean±S.E.M.). Letters indicate significant results of Fisher LSD post-hoc test.

STS Injury.

Primary rat cortical neurons were harvested and plated in neurobasal/B27 (+AO). At D.I.V. 11, ½ media was collected (conditioned media) and mixed with an equal volume fresh neurobasal media (to make the 24 hour treatment media). STS was prepared at the desired concentration in treatment media, with or without experimental drugs (AQ2S or LY294002). The remaining growth maintenance media was replaced with 100 µL of treatment media per well of a 96-well plate (or 2 mL for a six-well plate) for 24 hours. The results are shown in FIG. 5. Co-treatment with 75 µM AQ2S significantly reduced 24 hour STS injury determined by four different assays: resazurin metabolism (CellTiter Blue; FIG. 5a), LDH release (FIG. 5b), cellular ATP levels (GLO-Viability Assay; FIG. 5c), and live-cell protease activity (CellTiter-Fluor; FIG. 5d). AQ2S alone did not significantly alter baseline viability or cytotoxicity.

Cell Viability Assays.

CellTiter-Blue assay (PROMEGA) was prepared according to vendor instructions. The assay measures the ability of live cells to convert the reagent resazurin into its fluorescent form resorufin but does not kill the cells in the process, thus allowing for further downstream applications (e.g. caspase 3/7 activity assay). Briefly, 24 hours post-injury, 20 µL CellTiter Blue (warmed to room temperature) was directly added to each well of a 96-well plate. Plates were incubated in the dark for ~2 hours, and metabolism of resazurin measured using a fluorometric plate reader (Fusion™α, Packard). The CellTiter-GLO assay (PROMEGA) measures the amount of ATP in culture samples (equal to the number live cells) by induction of a luminescent signal. 100 µL CellTiter-GLO regent is added directly to each well of a 96-well plate as a terminal procedure (neurons are lysed). Luminescence was measured using a luminometer (Wallac 1420 Victor II multiwell counter, Perkin Elmer Life Sciences). In separate experiments, 100 µL of CellTiter-GLO assay reagent (Promega) was added directly to each well of a 96-well plate as a terminal procedure (neurons are lysed). ATP levels in live cells increase luminescence and was measured using a luminometer (Wallac 1420 Victor II multiwell counter, PerkinElmer Life Sciences). In separate experiments, 100 µL of CellTiter-Fluor assay reagent (Promega) was added directly to each well of a 96-well plate. Live-cell protease activity was measured by detection of free AFC reagent.

Caspase-GLO Luminescent Assay.

After viability was assessed (2 hours CellTiter-Blue incubation), 100 µL Caspase3/7-GLO regent was directly added to each well of a 96-well plate as a terminal procedure (neurons are lysed) and incubated for 1 hour. The Caspase3/ 7-GLO assay uses the exact same reagents as the CellTiter-GLO assay accept for the addition of a luciferin substrate crosslinked to an amino acid caspase cleavage target. Activation of caspases frees luciferin. Luciferin can then be oxidized by luciferase, thereby initiating a light reaction. Luminescence was measured using a luminometer. In separate experiments, 100 µL caspase 8-GLO and Caspase 9-GLO reagents were added to each well of a 96-well plate.

Lactate Dehydrogenase (LDH) Assay.

The LDH Cytotoxicity Assay Kit II was purchased from Abcam (Cambridge, Mass., USA). Neurons were cultured in 96-well format and subjected to STS injury ±AQ2S for 24 hours (in 100 µL total media volume). At 23 hours maximum LDH release (positive control) was prepared by adding 10 µL cell lysis reagent directly to a few non-injured wells (i.e., no STS or AQ2S). At the end of the 24 hour injury period, 80 µL of media was transferred to a new 96-well plate. Plates were spun at ~500 g for 5 minutes. 10 µL of cell culture treatment media was added to a new black-walled plate and advanced WST detection reagent added. The mix was incubated for ~15 minutes and absorbance measured (OD 450 nm). Fresh culture media was used as a negative control. Cytotoxicity was calculated using the standard formula: cytotoxicity %=(sample LDH−negative-control LDH)/(maximum LDH release−negative-control LDH)×100.

TUNEL Analysis.

Neurons were grown on poly-D-lysine/laminin 8-well culture slides (BD Biosciences). Neurons were treated with 50 µM $H_2O_2$ using the above described methods. After 24 hours injury, neurons were rinsed once in ice cold PBS, and incubated in 4% paraformaldehyde for 25 minutes at 4° C. Slides were prepared for TUNEL analysis using vendor kit/protocol (Dead End Fluorometric TUNEL kit; PROMEGA). Slides were mounted in solution containing DAPI. TUNEL positive nuclei glow green under fluorescent microscope (Eclipse 50, Nikon). Data was collected and analyzed as follows. Three random field images from a single well (i.e. n=1 for data analysis) on an 8-well culture slide were captured under 20× objective using SPOT software (SPOT, RTke Diagnostic Instruments). Nuclei stain blue (i.e. DAPI) and TUNEL positive nuclei stain green. Corresponding DAPI/TUNEL images were overlaid in photoshop, and a random ~0.250 mm$^2$ area selected for counting. This procedure was repeated 3 times for each treatment group (i.e. n=1; 3 DAPI images and 3 TUNEL images). The % TUNEL positive nuclei was calculated from each DAPI/TUNEL pair, and the 3 values averaged together (n=1). The process was repeated for all 6 wells, and the data analyzed using an unpaired T-test.

Caspase-3 Drug Screening Assay.

An in vitro caspase drug screening kit was purchased from PromoKine (Heidelberg, Germany), and used according to the manufacturer's instructions. Briefly, all drugs were dissolved in DMSO and diluted in double-distilled water to desired concentration. The reaction mixture was combined with recombinant active caspase-3 and a DEVD-AFC probe. Active caspase-3 cleaves the DEVD-recognition sequence and releases fluorescent AFC. The amount of AFC detected is a measure of caspase-3 activity. Reactions were prepared in black-walled 96-well plates, incubated at 37° C., and AFC release measured with an AFC filter (Ex: 405 nM, Em: 495-505 nM) on a GLOMax-Multi Microplate Reader (Promega). A single data point (value=15.51462) in the caspase-3 control (no inhibitor) group (data set: mean=40.60833 and S.D.=10.67385) was removed from statistical analysis. The value was a significant outlier (P<0.05), as determine by the Grubbs' test.

Western Blot Analysis.

Neurons used for Western blot analysis for grown in 6-well plates. Briefly, neurons were treated with experimental compounds for the indicated time/conditions. At the end of each experiment, neurons were washed in ice cold PBS and harvested in 65 µL RIPA buffer containing protease inhibitors, phosphatase inhibitors, and EDTA. Extracts were collected in 0.5 mL tubes and sonicated for 20-30 seconds. Cell extracts were then spun at 4° C./16,000 g/10 minutes and stored at −80° C. until use. Frozen extracts were thawed on ice and protein concentration measured using the BCA assay (PIERCE). 10-20 µg of sample protein was loaded per well of a 7.5% SDS precast gel (Biorad), and run for 30 minutes to 1 hour at 200 V. Kaleidoscope protein standards (Biorad) were run parallel to neuron extracts. Proteins were then transferred to PDVF membranes (run at 100 V/4° C./1.5 hours). PDVF membranes were washed once in tris buffered saline (TBS) and blocked for 1 hour in tris buffered saline/tween-20 with 7.5% nonfat milk (TBS-T/milk). Blots were incubated overnight at 4° C. with primary antibodies in TBS-T/milk. Cell Signaling Technology: phospho-AKT473, AKT Total, phospho-ERK1/2, ERK Total, cleavage caspase-3. Santa Cruz Antibodies: NF-κB p50 subunit, NF-κB p65 subunit, and beta actin. Calbiochem: 4-HNE antibody. Blots were washed 3 times (5 minutes each) with TBS, and incubated with secondary antibodies for 2 hours. Invitrogen: goat anti-rabbit or goat anti-mouse. Blots were washed 3 times (5 minutes each) with TBS, and incubated for 1 minute in HRP detection solution (Amersham). Films were exposed to blots and developed (SRX-101A, Konica Minolta Medical & Graphic Inc.). Re-probed blots (e.g. beta actin, AKT total, ERK total) were stripped in western blot stripping buffer (Fischer Scientific) for 10 minutes, washed once with TBS, re-blocked in TBS-T/milk for 1 hour, and incubated overnight with new primary antibody. Films were scanned (EPSON GT 20,000), and densitometry performed using UN-SCAN-IT software (Silk Scientific).

Statistics. Data was graphed using GraphPad Prism (GraphPad Software Inc.) GraphPad statistical software was used to perform unpaired T-test analysis. NCSS statistical software (NCSS) was used for One-Way-Analysis-of-Variance (One-way-ANOVA). If a data set had large unequal variances, the data was first transformed to log base 10 values, and the transformed values analyzed using NCSS. Data are significant at p<0.05.

Stretch-TBI Methods

Background: Traumatic brain injury (TBI) induces multiple cell death mechanisms. One key characteristic that distinguishes it from other injury modalities is the physical shearing/stretch injury component. The in vitro stretch injury paradigm is an accepted method to replicate the mechanical injury component of TBI.

Methods: Rat cortical neurons are isolated from E16 embryos, and plated on silicone membranes (with defined elastic properties) held in a custom made stainless steel chamber. DIV 7-9 neurons are subjected to a (computer controlled) preset stretch injury; strain rate $10s^{-1}$ and 50% membrane deformation. AQ2S or DMSO (vehicle control) was added before (pre-treatment) or after post-treatment) injury, Cell death was assayed ~24 hours after injury by measuring 1) extracellular LDH in the culture media (released from dying/dead cells), 2) caspase-3/7 activation (a protease involved in execution of cell death), and 3) MTT metabolism (a reagent metabolized by living cells).

Results: 1) Effect of AQ2S on Stretch Injury Induced Neuronal Lactate Dehydrogenase (LDH) Release. LDH is released by dying or injured cells. Primary rat cortical neurons were grown on a custom made stretch-injury device (An in vitro model of TBI). Neurons were pre-treated with 75 µM AQ2S or vehicle only (DMSO control) for 30 minutes, and subjected to a defined stretch injury. 24 hours after injury LDH levels were measured. The results of two separate experiments are shown in FIGS. 18A and 18B. AQ2S significantly reduced neuronal death (Experiment 1, n=8/treatment (FIG. 18A); Experiment 2, n=18/treatment (FIG. 18B)). Raw data was normalized to the average of three triton-X detergent treated wells (gives the values for 100% LDH release), and used to calculate percent LDH release after injury using the standard equation LDH Injury= (Treatment LDH—Control)/(Triton-X LDH—Control)× 100. Data was analyzed using a T-test; ***p<0.0001. Graphs show Mean+SEM.

2) Effect of AQ2S on Stretch Injury Induced Caspase3/7 Activity. Caspase activation plays a role in cell death after TBI. Primary rat cortical neurons were grown on a custom made stretch-injury device (An in vitro model of TBI). Neurons were pre-treated with 75 μM AQ2S or vehicle only (DMSO control) for 30 minutes, and subjected to a defined stretch injury. 24 hours after injury caspase3/7 activity was measured. The results of two separate experiments are shown in FIGS. 19A, B and C. AQ2S significantly reduced caspase activation (Experiment 1, n=6/treatment (FIG. 19A); Experiment 2, n=3/treatment (FIG. 19B)). (C) In a third experiment, AQ2S was administered 30 minutes before (pre-treatment) or 30 minutes after (post-treatment) stretch-TBI (FIG. 19C) (Experiment 3, n=3/treatment). Data was analyzed using ANOVA and Fisher LSD post-hoc test. Data is significant at (*) p<0.05. Graphs show Mean+SEM.

Figure 20:
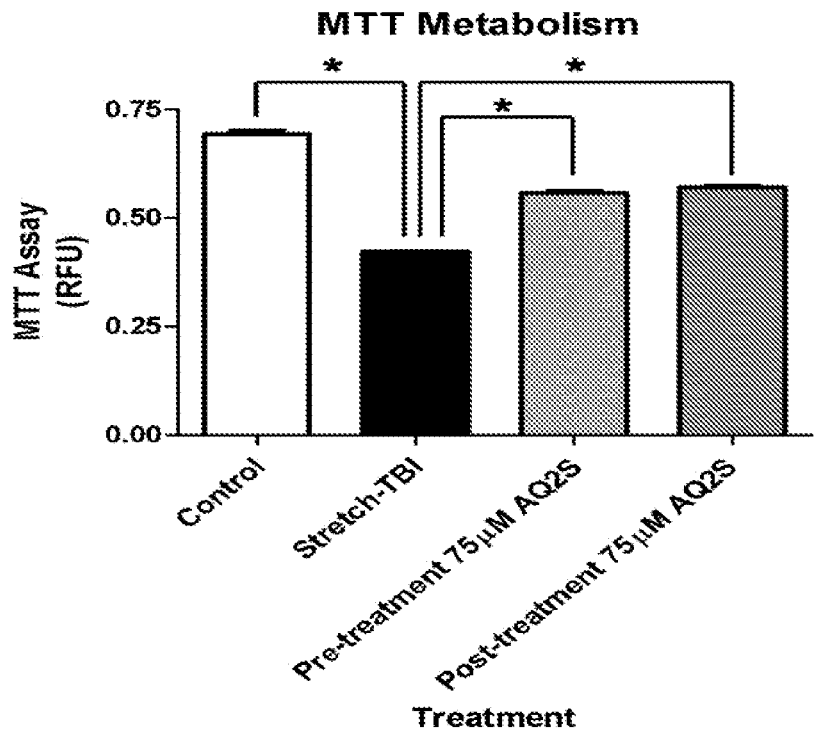
FIG. 20 is the effect of AQ2S on stretch injury induced reduction in 3-(4,5-dimethylthiazol-2-yl)-2,5-diphenyltetrazolium bromide (MTT) metabolism in primary rat cortical neurons.

3) Effect of AQ2S on Stretch Injury Induced Reduction in MTT Metabolism. (3-(4,5-Dimethylthiazol-2-yl)-2,5-diphenyltetrazolium bromide; MTT) is metabolized in living but not dying cells. Primary rat cortical neurons were grown on a custom made stretch-injury device (an in vitro model of TBI). Neurons were administered AQ2S 30 minutes before (pre-treatment) or 30 minutes after (post-treatment) a defined stretch injury (n=12/treatment). MTT metabolism was measured 24 hours after injury. FIG. 20 shows that MTT metabolism is significantly reduced by stretch-TBI injury, and increased by pre- or post-treatment with AQ2S. Data was analyzed using ANOVA and Fisher LSD post-hoc test. Data is significant at (*) p<0.05. Graphs show Mean+SEM.

Glutamate Injury Methods

Background: Excitotoxicity is a major mechanism of neuronal death in the brain. Glutamate is an excitatory neurotransmitter that regulates synaptic transmission (i.e. depolarization and action potential propagation). Glutamate binds ion gated channels in the extracellular space (e.g. NMDA receptors) and increases sodium and calcium flux across the membrane. Over activation of glutamate-gated ion channels induces neuronal death (i.e. excitotoxicity). This mechanism contributes to neuronal death in numerous acute and chronic brain conditions.

Methods: Drugs (AQ2S and MK801) were dissolved in 100% DMSO (vehicle). Rat cortical neurons were isolated from E17 embryos, and seeded onto 96-well plates at a density of $1.5 \times 10^5$/well. At day-in-vitro 8 (D.I.V. 8) culture maintenance media was replaced with treatment media (Modified Eagles Buffered Solution) without or with 5 μM Glutamate. After a 5 minute injury in treatment solution, cells were returned to normal culture maintenance media conditions (Neurobasal/B27 supplement) with either: 1) DMSO, 2) 125 μM AQ25 or 3) MK801; MK801 is an NMDA receptor channel blocker and classic neuroprotectant in this injury paradigm. Neuron viability was measured 24 hours post-injury by incubation with CellTiter Blue reagent (PROMEGA) for 2 hours. CellTiter Blue is metabolized into a fluorescent reagent only in living cells. The level of fluorescence (expressed as relative fluorescent units; RFU) was measured on a plate reader (PROMEGA).

Figure 21:
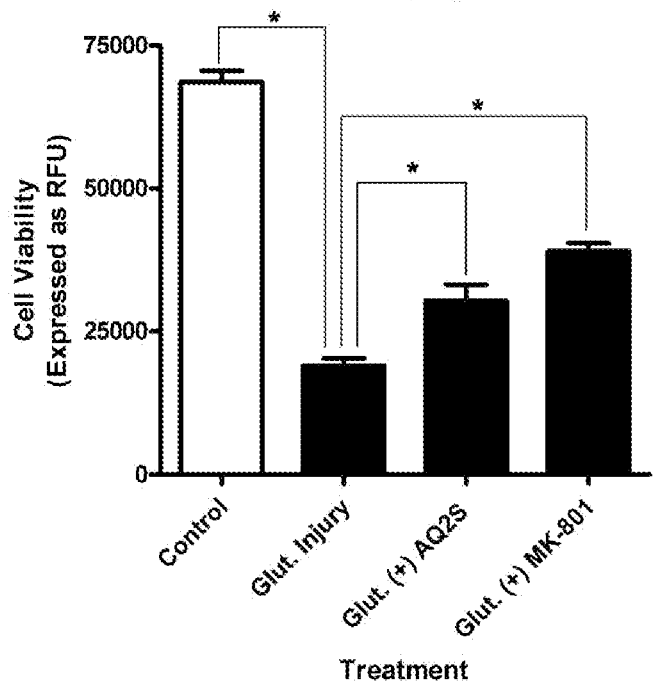
FIG. 21 is AQ2S mediated protection of primary rat cortical neurons against glutamate induced excitotoxic injury.

Results: AQ2S Protects Cortical Neurons from Glutamate Injury. Primary rat cortical neurons were grown onto 96-well plates. Neurons were treated with or without 5 μM glutamate. Cells were returned to regular growth media with DMSO, 125 μM AQ2S, or MK801 and viability measured 24 hours later (expressed as relative fluorescent units; RFU). FIG. 21 shows treatment conditions; replicates for Control (n=7), Glut. Injury (n=7), Glut+AQ2S (n=7) and Glut+MK-801 (n=6). White bar indicated absence of glutamate injury. Black bars indicate injured neurons. Data show that AQ2S significantly protects neurons from glutamate induced cell death. Data were analyzed by ANOVA (p<0.0001); Fisher LSD post-hoc test. * indicates p<0.05. Graphs show Mean+SEM.

Ischemia (OGD) Injury Methods

Background: Ischemia is a major cause of neuronal death in certain types of acute brain injury (e.g. stroke, cardiac arrest, asphyxia, hemorrhagic shock, severe hypotension). Ischemic injury can result from transient or pro-longed deleterious loss of adequate blood flow to vital organs/tissues. A key component of ischemic injury is loss of physiological oxygen and glucose supply. Ischemic injury can be replicated in vitro by subjecting cultured cells to pro-longed anoxia (no oxygen) and glucose deprivation.

Methods: AQ2S was dissolved in 100% DMSO (vehicle). Rat cortical neurons were isolated from E17 embryos, and seeded onto 96-well plates at a density of $7.5 \times 10^4$/well. At D.I.V. 10-11 culture maintenance media was replaced with treatment media (Modified Eagles Buffered Solution) without or with 25 μM Glucose. In addition, neurons were incubated with or without oxygen (induced by placement of cell plates in an anoxic chamber flushed with a gas mixture to remove oxygen). OGD injury was administered for 1 hour. After ischemic injury the treatment solution was removed and cells returned to normal culture maintenance media conditions (Neurobasal/B27 supplement) with either DMSO or 75 μM AQ2S, Neuron viability was measured 24 hours post-injury by incubation with CellTiter Blue reagent (PROMEGA) for 3.5 hours. CellTiter Blue is metabolized into a fluorescent reagent only in living cells. The level of fluorescence (expressed as relative fluorescent units; RFU) was measured on a plate reader (PROMEGA).

Figure 22:
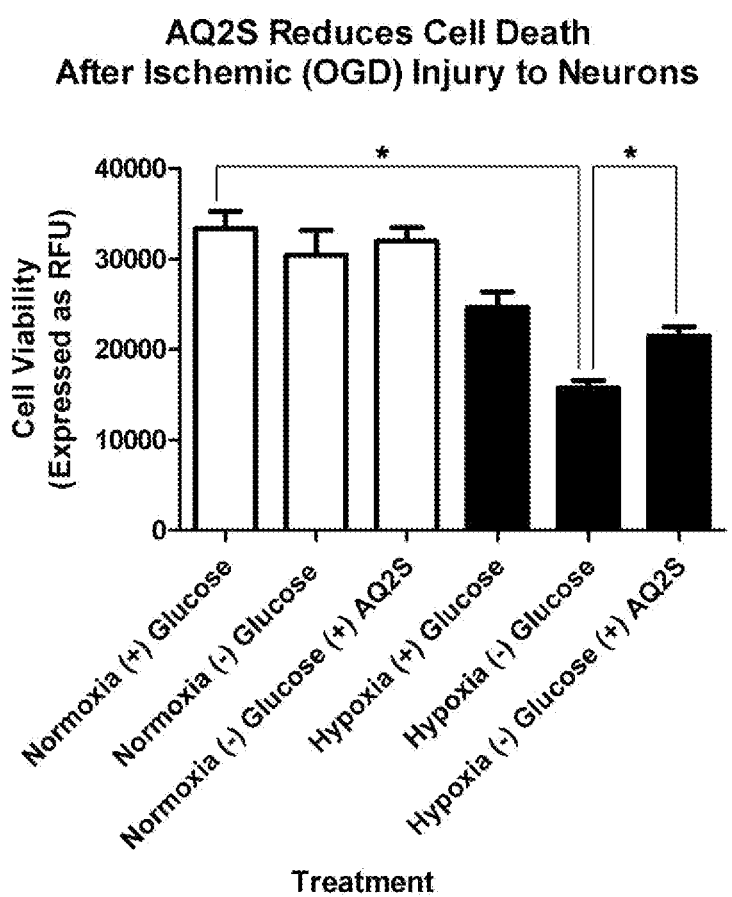
FIG. 22 is AQ2S mediated protection of primary rat cortical neurons from ischemic injury.

Results: AQ2S Protects Cortical Neurons from Ischemic Injury. Primary rat cortical neurons were grown onto 96-well plates. Neurons were injured by a 1 hour treatment with/without 25 μM glucose and with/without oxygen. DMSO or 75 μM AQ2S were added to OGD treatment media during the 1 h ischemic injury period. After 1 hour injury, cells were returned to regular growth media and normoxic culture conditions (i.e. 95% oxygen/5% $CO_2$) with either DMSO or 75 μM AQ2S. Cell viability was measured 24 hours later and expressed as relative fluorescent units (RFU). FIG. 22 shows treatment conditions (n=8 replicates for all groups). White bars indicate groups were treated 1 hour +/−glucose under normoxic conditions. Black bars indicate groups were treated 1 hour +/−glucose under hypoxic conditions. Data shows that combined oxygen/glucose deprivation (i.e. ischemia) maximally kills neurons. AQ2S significantly increases viability (i.e. protects) neurons from ischemic injury. Data were analyzed by ANOVA (p<0.0001); Fisher LSD post-hoc test. * indicates p<0.05. Graphs show Mean+SEM.

Controlled Cortical Impact (TBI) Injury Methods

Background: Traumatic brain injury (TBI) is a complex injury. Primary (e.g. crushing/shearing forces) and secondary (e.g. brain edema, haemorrhage, excitotoxicity, apoptosis) cell death mechanisms contribute to the evolving damage. Controlled cortical impact (CCI) injury is a well-characterized and accepted method to recapitulate the sequela of TBI in vivo.

Methods: AQ2S was prepared in 2% DMSO in PBS (i.e. vehicle). C57BL6 mice were administered a severe CCI brain injury. Severe brain trauma was induced by a pneumatic impactor device that delivers a defined cortical injury (impact depth, 1.6 mm; impact velocity, 5 m/s). 15 minutes after injury animals were given a 5 µL intracerebroventricular injection with either vehicle (n=7) or 500 µM AQ2S (n=7). The 5 µL injection volume was delivered at a rate of 0.5 µL/minute. At the chosen therapy dose/volume we estimate that the final tissue AQ2S concentration would be in the ~71 µL range. This estimate was extrapolated from known total CSF volumes in mice (35 µL). Pardridge, W M. (1991) *Transnasal and intraventricular delivery. In Peptide Drug Delivery to the Brain*, Raven Press, New York, pp. 99-122. A second vehicle or AQ2S injection was administered 24 hours after injury. Sham control animals (n=5) were given vehicle injections (15 minutes and 24 hours) but did not receive a CCI brain injury. 3 days after injury animals were sacrificed, perfused with a fixative, brains sectioned, and stained with hematoxylin and eosin (H&E). Images were captured using a light microscope and camera.

Figure 23:
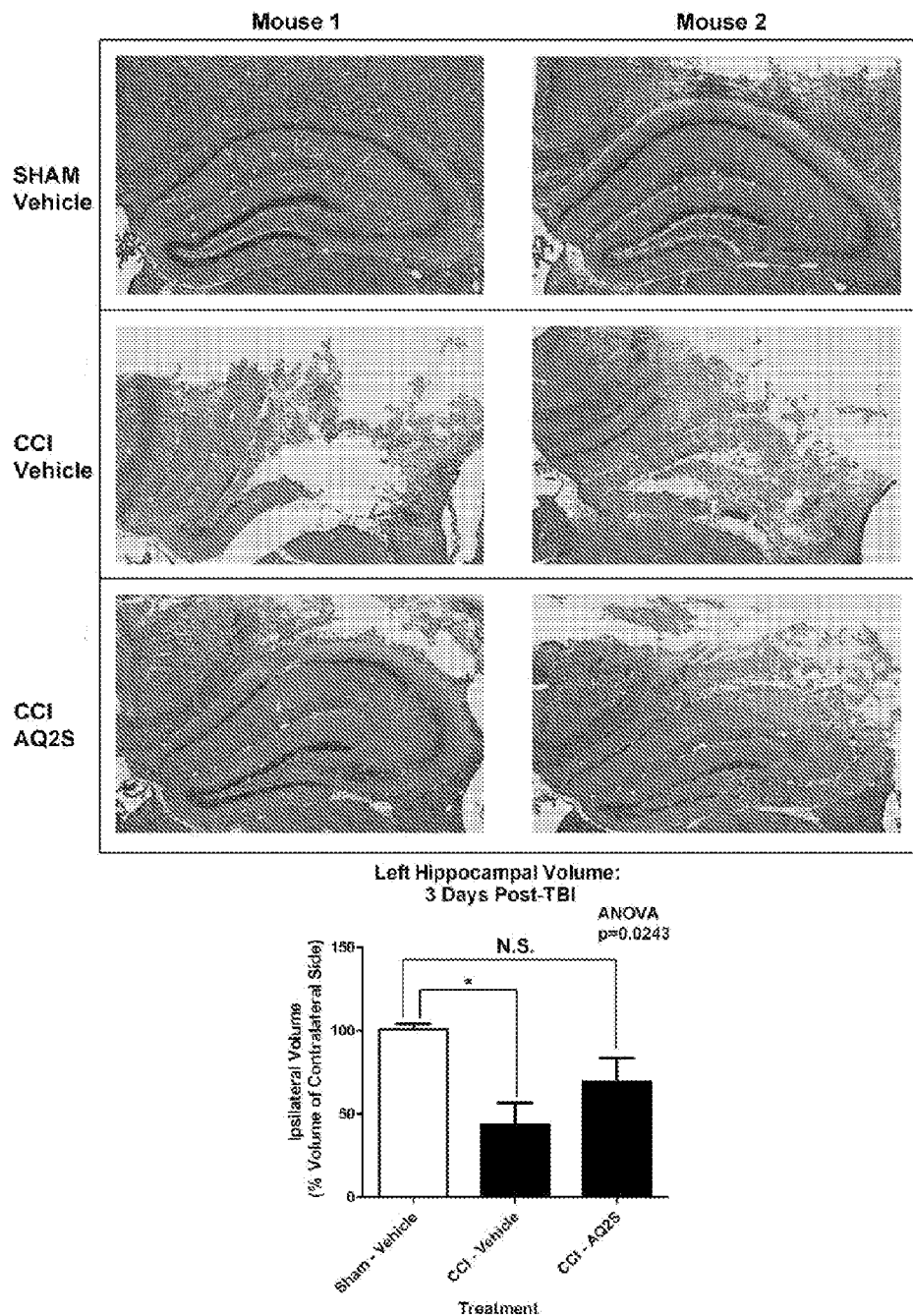
FIG. 23 is the AQ2S mediated decrease of total hippocampal damage in mice administered severe traumatic brain injury (TBI).

Results: AQ2S Therapy Decreases Hippocampal Damage after TBI. Mice were given surgical/treatment protocols and hippocampal tissue analyzed 3 days later. Representative histology in FIG. 23 (n=2/group) showing H&E tissue staining in (A) sham (non-injured) vehicle injected, (B) CCI injured vehicle injected, and (C)CCI injured AQ2S injected mice. (D) Left (injured) and right (non-injured) hippocampal volumes were quantified for each mouse; sham (n=5), vehicle CCI injury (n=7), and AQ2S CCI injury (n=7). FIG. 23D show left hippocampal volumes (expressed as % of uninjured right hippocampus). As expected, CCI significantly reduced left hippocampal volumes in vehicle treated mice. However, left hippocampal volumes were not significantly (N.S.) different from Sham animals in AQ2S treated mice (indicating tissue sparing). Data were analyzed by ANOVA (p=0.0243); Newman-Keuls Multiple Comparisons post-hoc test. (*) indicates p<0.05. Graphs show Mean+SEM.

Ventricular Fibrillation Cardiac Arrest (VF CA) Injury Model Methods

Background: Cardiac arrest induces widespread ischemic injury to the brain and other critical organ systems. Cognitive impairment and hippocampal cell death are key sequela of VF CA injury. New therapies to target these complications are desperately needed. AQ2S is an RBM5 inhibitor. RBM5 is a known pro-death protein, and may contribute to ischemic brain injury. It is unknown if RBM5 levels change in the brain after injury.

Methods: An established model of VF CA in rats was used, a model that reproducibly produces neuronal death in the CA1 region of the hippocampus. Adult SD rats (250-350 g) were anesthetized and placed on a respirator (30% oxygen). A 12 V/50 Hz alternating current was continually applied via a transesohageal electrode, inserted via the jugular vein, over a 2 minute period. VF CA was allowed to continue for a total of 6 minutes. CA was verified by ECG and blood pressure recordings. The electrode was removed and rats administered CPR (51 defibrillation) to initiate return of spontaneous circulation (ROSC). Epineprhine (0.02 mg/kg) was administered iv. Animals were then allowed to recover. Sham animals received surgical manipulations but did not get VFCA. 24 hours later sham and VFCA injured rats were sacrificed by isoflurane overdose, brains quickly isolated, and hippocampi snap-frozen in liquid nitrogen. Samples were stored at −80° C. until homogenization for biochemical analysis of RBM5.

Figure 24:
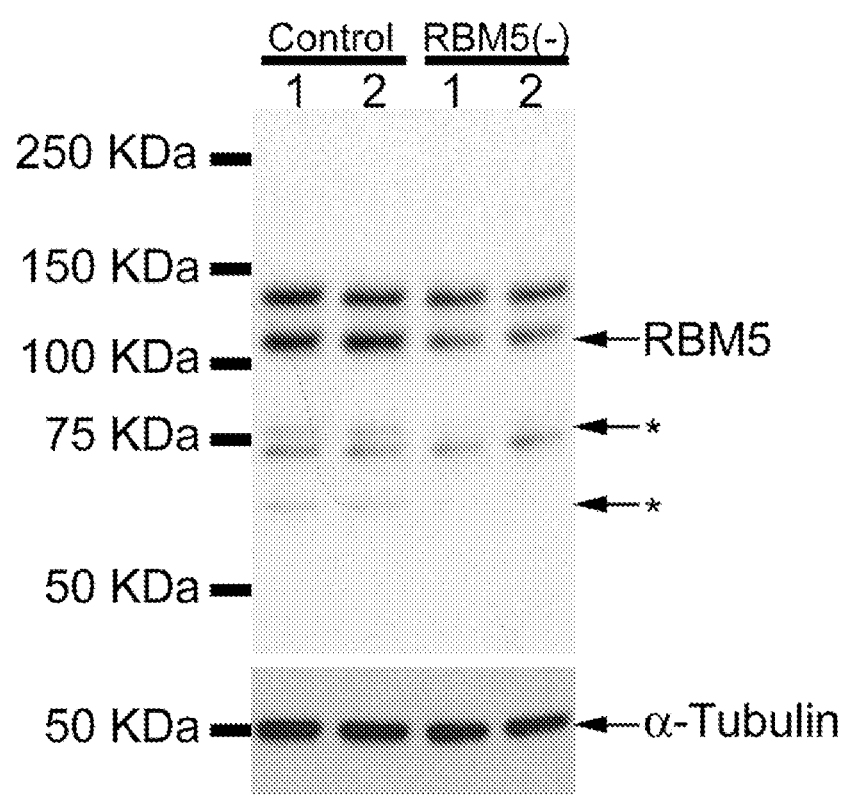
FIG. 24 is the validation of RBM5 antibody in human derived embryonic kidney (HEK) cells.

Results: Validation of RBM5 Antibody. FIG. 24 shows the results of the AQ2S antibody validation assay. Human derived embryonic kidney (HEK) cells were transduced with lentivirus. The lentivirus was designed to deliver a short hairpin RNA (shRNA) that selectively binds to RBM5 messenger RNA. Binding of RBM5 targeting shRNAs to endogenous RBM5 mRNA prevents protein translation. Therefore endogenous protein levels of RBM5 should decrease by this molecular targeting strategy. A commercial antibody predicted to detect RBM5 protein was purchased and probed in Control (i.e. HEK cells transduced with a virus that delivers a non-gene targeting shRNA) or RBM5 KO cells. Western blotting of harvested protein samples above show (in duplicate experiments) that the parent RBM5 protein (~120 KDa) is decreased after knockdown (indicating that this antibody is indeed detecting RBM5). (*) indicates possible RBM5 cleavage products or splice variants because they are also decreased by KO.

Figure 25:
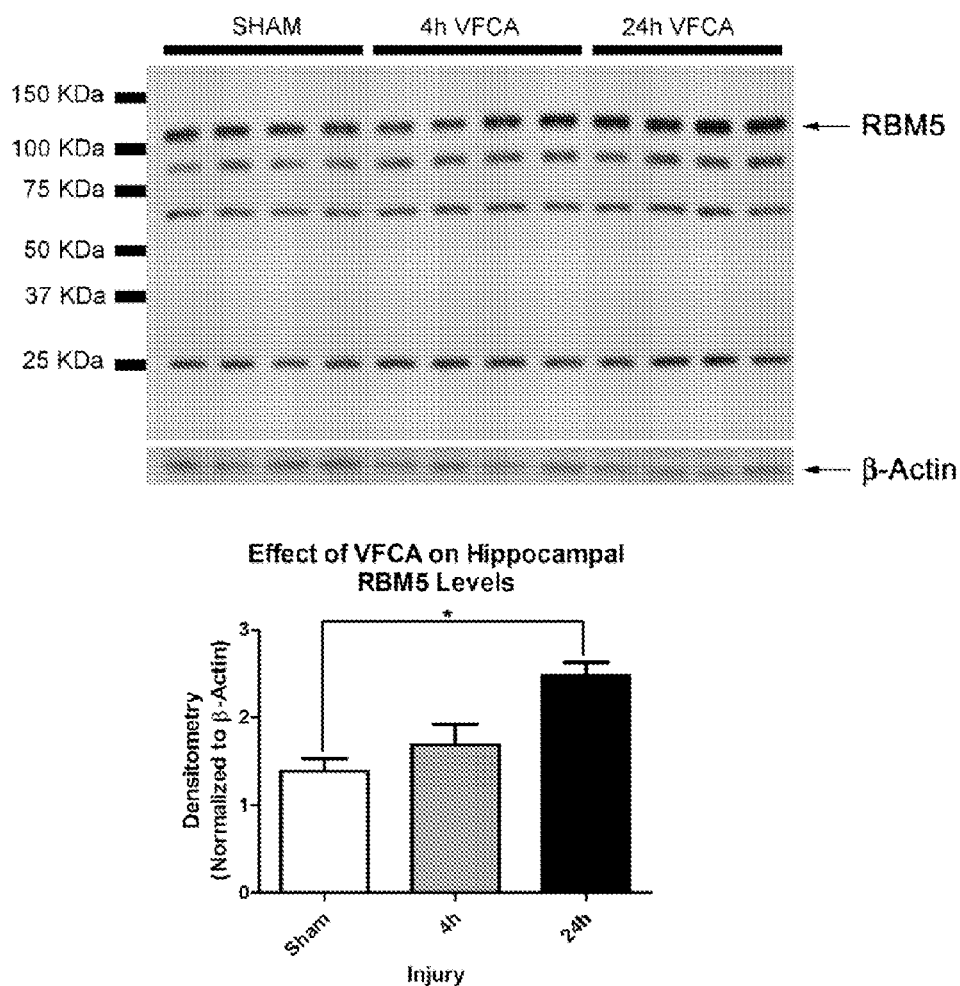
FIG. 25 is the increase in RBM5 levels in the hippocampus 24 hours after ventricular fibrillation cardiac arrest induced ischemic brain injury.

VF CA Increases RBM5 Levels in the Hippocampus 24 h after Injury. FIG. 25A shows a western blot of RBM5 levels in rat hippocampi protein extracts 4 hours (n=4 rats) and 24 hours (n=4 rats) after a 6 minute VF CA. Sham animals did not receive VF CA (n=4 rats). IG 19B shows semi quantification of western blot results. Densitometry show that the AQ2S target RBM5 significantly increases in the hippocampus 24 hours after a 6 minute CA brain injury. Data were analyzed by ANOVA (p<0.0001); Fisher LSD post-hoc test. * indicates p<0.05. Graphs show Mean+SEM.

N2a Staurosporine (STS) Cell Death Assay

Background: Mouse neuroblastoma (N2a) cells are commonly used to study neuronal death and neuroprotection. Removing serum from the maintenance cell growth culture media induces N2a differentiation into a more neuronal phenotype. Because they are highly amendable to molecular manipulation (e.g. virus mediated alteration in gene expression), we investigated the effect of RBM5 KO in these neuron-like cells.

Methods: Preparation for RBM5 KO Neuroprotection Experiment: N2a cells were grown in 10% Fetal Bovine Serum (FBS) dissolved in Dulbecco's Modified Eagle Medium (DMEM). At the time of viral infection (i.e. transduction), cells were removed from growth plates, and introduced onto new 10 cm culture plates. Cells were infected (i.e. transduced) with lentivirus in order to deliver either control (non-gene targeting shRNAs) or RBM5 targeting shRNAs. 24 hours later cells were given fresh media containing 10 µg/mL puromycin. Puromycin normally kills cell. However, our viruses also deliver a gene that confers cells resistant to death by the compound puromycin. This procedure called "selection" ensures that the only RBM5 KO (or control shRNA) cells are left alive (i.e. a near-pure population of genetically manipulated cells). After 48 hours of puromycin selection, cells were transferred onto a 96 well assay plate (in preparation for STS induced cell death) and allowed to proliferate another 24 hours in standard growth maintenance media. STS Neurotoxicity: The cells were washed twice with basal DMEM media (i.e. no serum added), and then cultured in serum free DMEM for 8 hours prior to the assay (to induce neuronal phenotype differentiation). The toxic compound staurosporine (STS) was dissolved/prepared in 100% DMSO. N2a-Control cells and N2a-RBM5 KO cells were treated 18 hours with either DMSO (vehicle control), 100 nM staurosporine or 500 nM staurosporine in serum free DMEM. Viability was measured by CellTiter Blue metabolism (PROMEGA) and analyzed on a plate reader (PROMEGA). Viability results expressed as relative fluorescent units (FRFU). Live cell images were obtained by brightfield photography using a 20× scope with a digital camera attachment.

Results: RBM5 KO Protects N2a Cells from STS Induced Cell Death. N2a cells were transduced with lentivirus and delivered either control (non-gene targeting) or RBM5 targeting shRNAs (same RBM5 targeting sequence used for KO in HEK cells; see FIG. 24. The cells were treated with DMSO (vehicle control), 100 nM staurosporine or 500 nM staurosporine in serum free media for 18 hours. FIG. 26A shows representative Brightfield (live) cell images showing the effect of 100 nM STS on control and RBM5 KO cells. Control cells treated with 100 nM staurosporine (STS) are noticeably fewer compared to RBM5 KO cells. The graph in FIG. 26B compares the viability of N2a-control vs. N2a-KO cells treated +/−STS for 18 hours. Viability is expressed as relative fluorescent units (RFU). Numbers above the individual bars indicate the percentage of cells alive (relative to each virus' respective DMSO control). The data show that the RBM5 knockdown cells were more resistant to cell death when compared to the control cells. Data were analyzed by ANOVA ($p<0.001$) and Fishers LSD post-hoc T-Test. For all groups n=8, * indicated $p<0.05$. Graphs show Mean+SEM.

Figure 27:
FIG. 27 is the RBM5 levels in young and adult rats.

RBM5 Levels in Young and Adult Rats. Brain sections (in different brain regions) from adult animals and postnatal day 17 (PND17) young animals were stained using the validated RBM5 antibody (FIG. 27). RBM5 (brown staining) was highly abundant in neurons but also expressed at lower levels in glial cells in both adult and young animals. However, RBM5 levels were much higher in young animals. The results indicate that young patients (i.e. pediatric) may be an important sub-population that may maximally benefit AQ2S therapy.

Staurosporine (STS) Injury in Human Heart Cells

Background: Results presented herein show that AQ2S therapy reduces staurosporine (STS) cell death in primary rat cortical neurons, but AQ2S can protect non-CNS tissues as well (and in humans).

Methods: Human derived myocardial heart cells were seeded onto 96-well plates. 24 hours later cells were injured with STS. 24 hour co-treatment with STS and AQ2S in heart cells increased viability (as measured by CellTiter Blue metabolism).

Results: AQ2S Protects Human Heart Cells from STS Induced Injury. Optimal cell death conditions were established in heart cells. Heart cells were treated with STS at increasing doses for 24 hours (FIG. 28A). FIG. 28B shows the effect of AQ2S on heart cell viability. Heart cells were treated with 500 nM STS+/−125 µM AQ25 or 1 µM STS+/−125 µM AQ2S for 24 hours. Cell viability was measured 24 hours later and expressed as relative fluorescent units (RFU). The graph shows treatment conditions (n=8 replicates for all groups except the 1 µM STS+125 µM AQ2S group; n=7). Data were analyzed by ANOVA ($p<0.0001$); Fisher LSD post-hoc test. * indicates $p<0.05$. Graphs show Mean+SEM.

In view of the many possible embodiments to which the principles of the disclosed compounds, compositions and methods may be applied, it should be recognized that the illustrated embodiments are only preferred examples and should not be taken as limiting the scope of the invention.

What is claimed is:

1. A method for treating a brain injury in a subject comprising administering to a subject in need thereof a therapeutically effective amount of
   anthraquinone-2-sulfonic acid, or a pharmaceutically acceptable salt or ester thereof.

2. The method of claim 1, wherein the brain injury is an acute brain injury or a traumatic brain injury.

3. The method of claim 2, wherein the acute brain injury is caused by stroke, cardiac arrest, asphyxia, hemorrhagic shock, subarachnoid haemorrhage, or severe hypotension.

4. The method of claim 1, wherein the brain injury is caused by ischemia.

5. The method of claim 1, wherein the compound is administered post-injury.

6. The method of claim 1, wherein the subject is administered anthraquinone-2-sulfonic acid.

7. The method of claim 1, wherein the brain injury is caused by blunt trauma, penetrating trauma, or blast trauma.

* * * * *